(12) United States Patent
Risby et al.

(10) Patent No.: US 6,248,078 B1
(45) Date of Patent: Jun. 19, 2001

(54) VOLATILE BIOMARKERS FOR ANALYSIS OF HEPATIC DISORDERS

(75) Inventors: Terence H. Risby, Cockeysville; Shelley Sehnert, Baltimore, both of MD (US); Long Jiang, Ottawa (CA); James F. Burdick, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/385,657

(22) Filed: Aug. 27, 1999

Related U.S. Application Data

(63) Continuation of application No. 60/098,467, filed on Aug. 31, 1998.

(51) Int. Cl.⁷ ..................................................... A61B 5/08
(52) U.S. Cl. ........................ 600/529; 600/532; 600/543; 73/23.3
(58) Field of Search .................................... 600/529, 531, 600/532, 533, 537, 538, 539, 540, 541, 542, 543; 73/23.3

(56) References Cited

U.S. PATENT DOCUMENTS

| | | |
|---|---|---|
| 3,613,665 | 10/1971 | Gorsuch . |
| 3,622,278 | 11/1971 | Elzinga et al. . |
| 5,042,501 | 8/1991 | Kenny et al. . |
| 5,309,921 * | 5/1994 | Kisner et al. ........................ 600/532 |
| 5,386,832 * | 2/1995 | Wagner et al. ....................... 600/532 |
| 5,425,374 | 6/1995 | Ueda et al. . |
| 5,510,269 | 4/1996 | Black et al. . |
| 5,515,859 | 5/1996 | Paz . |
| 5,525,799 | 6/1996 | Andresen et al. . |
| 5,573,005 | 11/1996 | Ueda et al. . |
| 5,754,288 * | 5/1998 | Yamamoto et al. ................. 356/301 |
| 5,802,909 | 9/1998 | Faulder et al. . |
| 5,807,750 | 9/1998 | Baum et al. . |
| 5,928,167 * | 7/1999 | Wagner et al. ....................... 600/584 |
| 5,929,319 | 7/1999 | King et al. . |
| 5,961,470 * | 10/1999 | Wagner et al. ....................... 600/532 |
| 6,057,162 * | 5/2000 | Rounbehler et al. ................. 73/23.3 |
| 6,110,122 * | 8/2000 | Wagner et al. ....................... 600/532 |

FOREIGN PATENT DOCUMENTS

WO 97/00443   1/1997   (WO) .

OTHER PUBLICATIONS

Hotz, et al., "Development Of A Method To Monitor Low Molecular Mass Hydrocarbons In Exhaled Breath Of Man: Preliminary Evaluation Of Its Interest For Detecting A Lipoperoxidation Process In Vivo", *Clinica Chimica Acta*, vol. 162, pp. 303–310 (1987).

(List continued on next page.)

Primary Examiner—Cary O'Connor
Assistant Examiner—Navin Natnithithadha
(74) Attorney, Agent, or Firm—Edwards & Angell, LLP; Linda M. Buckley; Robert L. Buchanan

(57) ABSTRACT

The present invention features test systems and methods for detecting a hepatic disorder in a mammal and especially a primate. Preferred use of the invention involves staging the hepatic disorder in a human patient.

56 Claims, 8 Drawing Sheets

OTHER PUBLICATIONS

Lettéron, et al., "Increased Ethane Exhalation, An In Vivo Index Of Lipid Peroxidation, In Alcohol Abusers", *Gut*, vol. 34, pp. 409–414 (1993).

Risby, et al. "Evidence For Free Radical–Meidated Lipid Peroxidation At Reperfusion Of Human Orthotopic Liver Transplants", *Surgery*, vol. 115, No. 1, pp. 94–101 (1994).

Lee, et al., "Tunable Diode Laser Spectroscopy For Isotope Analysis—Detection Of Isotopic Carbon Monoxide In Exhaled Breath", *IEEE Transactions On Biomedical Engineering*, vol. 38, No. 10, pp. 966–973 (1991).

Witschi, et al. "Mitochondrial Function Reflected By The Decarboxylation Of [13C]Ketoisocaproate Is Impaired In Alcoholics", *Alcoholism: Clinical and Experimental Research*, vol. 18, No. 4, pp. 951–955 (1994).

Kazui, et al. "Visceral Lipid Peroxidation Occurs At Reperfusion After Supraceliac Aortic Cross–Clamping", *Journal of Vascular Surgery*, vol. 19, No. 3, pp. 473–477 (1994).

Miller, III, et al. "Association Between Cigarette Smoking And Lipid Peroxidation In A Controlled Feeding Study", *Circulation*, vol. 96, No. 4, pp. 1097–1101 (1997).

McManus, et al. "Astigmatic Mirror Multipass Absorption Cells For Long–Path–Length Spectroscopy", *Applied Optics*, vol. 34, No. 18, pp. 3336–3348 (1995).

Jay A. Perman "Clinical Application Of Breath Hydrogen Measurements", *Can J. Physiol. Pharmacol.*, vol. 69, pp. 111–115 (1991).

Copy of International Search Report dated Dec. 23, 1999 re Int'l Appln. No. PCT/US99/19552 (six pages).

Arterberry, et al., *Free Radical Biology & Medicine*, 17:6, 569–579 (1994).

Chen, et al., *J. Lab. Clin. Med.*, 75:4, 628–635 (1970).

Kaji, et al., *Clinica Chimica Acta*, 85:279–284 (1978).

Kazui, et al., *Free Radical Biology & Medicine*, 13:509–515 (1992).

Michael Phillips, *Scientific American*, 74–79 (1992).

Phillips, et al., *J. of Chromatography*, 422:235–238 (1987).

Phillips, et al., *Analytical Biochemistry*, 163:165–169 (1987).

Phillips, et al., *J. Clin. Pathol.*, 46:861–864 (1993).

Phillips, et al., *Clin. Chem.*, 38/1:60–65 (1992).

Phillips, et al., *J. of Chromatography*, 564:242–249 (1991).

Tangerman, et al., *Clinica Chimica Acta*, 130:103–110 (1983).

Tangerman, et al., *J. Lab. Clin. Med.*, 175–182 (1985).

Taucher, et al., *Rapid Communications in Mass Spectrometry*, 11:1230–1234 (1997).

\* cited by examiner

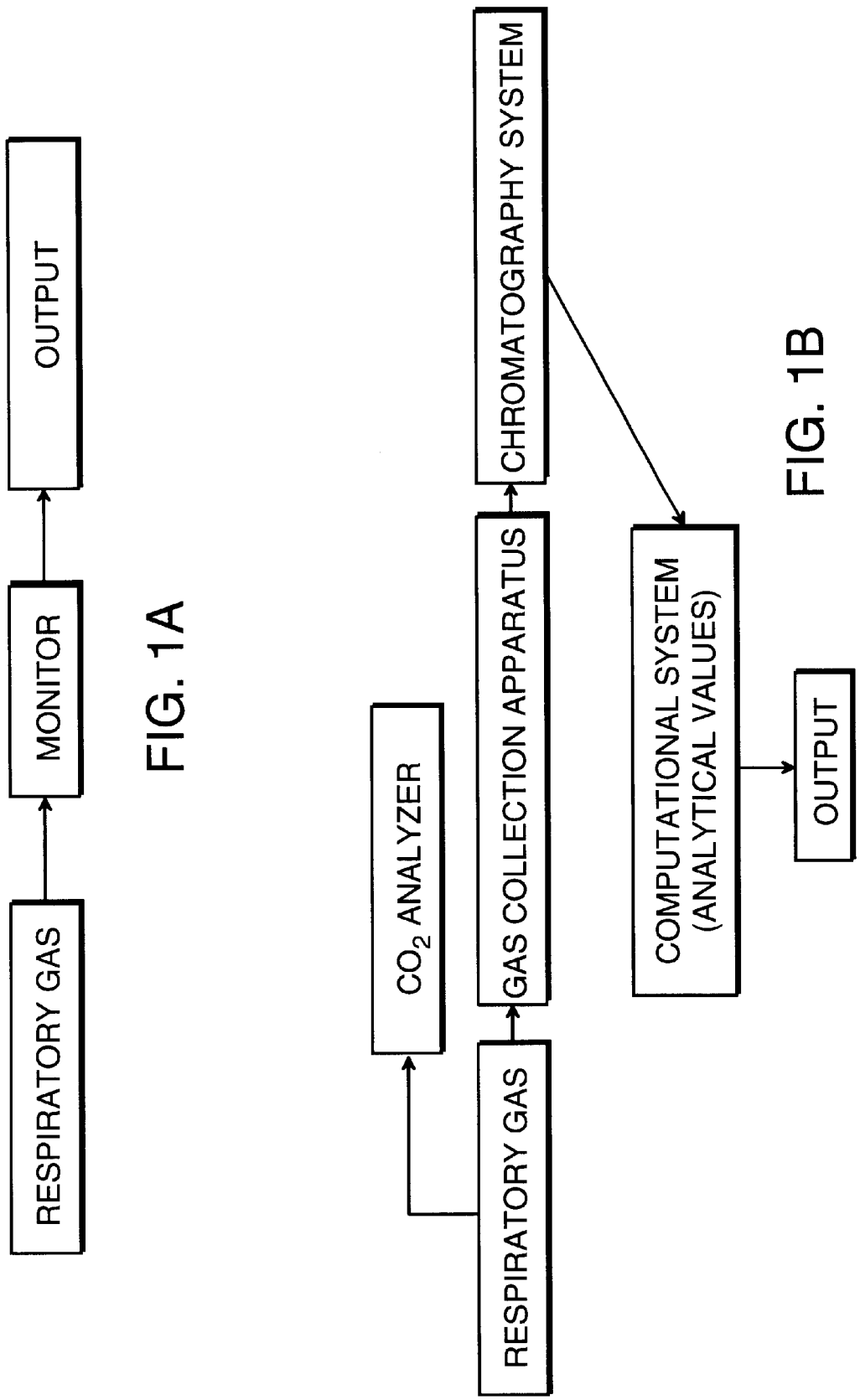

VOLATILE BIOMARKERS FOR ANALYSIS OF HEPATIC DISORDERS

CROSS-REFERENCE TO RELATED APPLICATION

The present application is a continuation of U.S. Ser. No. 60/098,467 filed on Aug. 31, 1998; the disclosure of which is hereby incorporated by reference.

STATEMENT OF GOVERNMENT INTEREST

Funding for the present invention was provided in part by the Government of the United States by virtue of Grant No. F49620-95-1-0270 from the U.S. Air Force. Thus, the Government of the United States has certain rights in and to the invention claimed herein.

FIELD OF THE INVENTION

The present invention generally relates to analysis of hepatic disorders in a mammal. For example, in one aspect, the invention relates to test systems and methods for detecting and/or staging hepatic disorders in a human patient. The present invention is useful for a variety of applications including use in the diagnosis or treatment of liver disease.

BACKGROUND

There is recognition that a variety of methods can be used to detect hepatic disorders particularly in human patients. The methods are generally dominated by fluid-based tests that monitor liver-related molecules in blood, plasma and urine. See e.g., *Handbook of Clinical Laboratory Data* (1997) (CRC Press, Inc. West Palm Beach, Fla.)

However, many of the fluid-based tests for hepatic dysfunction are believed to be associated with significant drawbacks. For example, most of the tests are optimized to provide only an indirect measure of liver function. That is, the tests provide little or no information about how the liver functions in real-time. Significant patient follow-up and testing is often needed to achieve desired results. Additionally, there has been some concern that fluid-based tests may not always provide enough sensitivity or selectivity to detect mild hepatic disorders. Nearly all of the tests require handling of body fluids, thereby posing a biohazard risk to personnel conducting the tests.

Several attempts have been made to provide more effective methods for detecting hepatic disorders. For example, in one approach, a biopsy is taken from the patient to more precisely evaluate liver function. However, biopsy procedures are often costly, time-intensive and extremely painful. Biopsy procedures may also be unsuitable for patients suffering from specific hepatic disorders or patients who have received a liver transplant.

In another approach, it has been reported that it is possible to relate presence of certain volatile molecules in human breath to specific conditions. Several tests have been designed to detect these molecules. See e.g., Phillips, M., *Sci. Am.*, (1992), 267: 74; Perman, J. A., *Canad. J Physiol. Pharmac.*, (1991); 69: 111; Risby et al., *Surgery,* (1994), 115, 94; and Kazui et al., *Free Radic Biol. Med.,* (1992), 13, 509; for disclosure relating to the prior breath tests.

More specific breath tests have been disclosed. For example, U.S. Pat. No. 5,386,832 discloses assays for measuring liver function by analyzing specific labeled molecules in human breath.

More particularly, it has been reported that specific sulfurous compounds such as volatile sulfides can be detected in the breath of some cirrhotic patients. It has been proposed that at least some of the compounds may arise from liver dysfunction. See e.g., Chen et al., *J. Lab Clin. Med.,* (1970), 75: 628; Kaji et al., *Clin. Chim. Acta,* (1978), 85: 279; Tangernan et al., *J. Lab Clin. Med.,* (1985), 106: 175 and Husamura, M., *Nippon Naisa Gakkai Zasshi,* (1979), 68: 1284.

However, the breath tests mentioned have been associated with problems which have tended to restrict use. For example, practically none of the tests are formatted to classify and/or stage a hepatic disorder. That is, the tests are not optimized to provide information as to what liver disorder is manifested by a patient and to what extent that disorder has progressed In addition, the tests usually cannot discriminate between different or closely related hepatic disorders. These shortcomings can negatively impact patient care in a variety of ways, e.g., by complicating diagnoses and/or delaying implementation of a life-saving therapy. The inability of the prior breath tests to stage hepatic disorders has made it especially difficult to evaluate patients in real-time.

Additionally, several of the prior breath tests have been reported to require administration of carbon 14 or other nuclides. Release of radioactive respiratory gas by patients may not be desirable for several reasons.

Many of the prior breath tests suffer from additional drawbacks and disadvantages. For example, as disclosed, the tests often require substantial breath samples, thereby restricting use to patients that can safely provide a substantial volume of breath. However, in many situations, patients may not be able to provide a large breath volume. Several specific breath tests require nearly all of the patient's breath sample, thereby eliminating opportunities to re-test the breath samples after analysis. In instances where more breath is needed, it can be very inconvenient or even impossible for patients to provide another breath sample. In cases where a patient's breath sample is exhausted, follow-up tests and statistical analyses can be difficult or impossible to perform, which compromises the accuracy of the analysis.

It has been disclosed that human breath includes perhaps hundreds of volatile organic molecules. However, only a fraction of these molecules are believed to relate to hepatic disorders. Accordingly, there is a need in the field to develop effective tests that can reliably characterize the disorders. In particular, it would be desirable to have test systems and methods that can facilitate reliable detection and preferably staging of hepatic disorders in a human patients.

SUMMARY OF THE INVENTION

The present invention generally relates to test systems and methods for characterizing a hepatic disorder in a mammal, and particularly a human patient. In general, the test systems and methods detect at least one volatile organic molecule in respiratory gas and relate the organic molecule to the presence and preferably the stage of the hepatic disorder in the mammal. The present invention has several important applications including use in the diagnosis and/or treatment of hepatic disorders in human patients.

More particularly, we have discovered that certain volatile organic molecules in respiratory gas can be used to detect and preferably stage a variety of hepatic disorders. Sometimes the volatile organic molecules will be referred to herein as breath "biomarkers" or a similar term to denote a physiological origin for these molecules. Preferred use of the invention generally involves detection and quantitation of biomarkers that have been found to be indicative of the presence and stage of certain hepatic disorders. For example, it has been found that the presence and stage of specific hepatic disorders can be determined with high sensitivity and selectivity by detecting and quantifying the biomarkers. Preferred use of the invention typically requires minimal breath volumes, thereby facilitating testing of sick, infirm or very young patients including children and infants. Patient inconvenience with respect to providing substantial breath samples is reduced or eliminated by the invention. The test systems and methods described herein are non-invasive and are well-suited for safe and reliable handling of a large numbers of breath samples.

The present invention has additional important uses and advantages. For example, it can be used to provide a reliable indicator of liver function at an early stage of disease progression and in real-time. Opportunities for early medical intervention are therefore increased. The invention can be used to monitor liver function in patients having or suspected of having a family history of liver disease. Alternatively, the invention can be used to evaluate liver function as part of a routine medical check-up. As a specific illustration, the invention can be used as part of a pre-natal care program to provide real-time analysis of liver function in a mother and her fetus. Other applications of the invention include use in veterinary settings to monitor liver function in domesticated or wild animals.

Accordingly, in one aspect, the present invention features test systems for detecting and preferably staging a hepatic disorder in a mammal such as a human patient.

In one embodiment, the invention features a test system that includes at least one and preferably all of the following components:

a) a chamber for receiving respiratory gas from the mammal; and b) a monitor for detecting at least one volatile organic molecule in the respiratory gas and for outputting the concentration of at least one of the detected organic molecules, e.g., to an apparatus or to an operator as a display.

In one embodiment, the chamber is a conventional chamber suited to receive the respiratory gas and especially breath from a human patient. In a particular embodiment, the monitor is a standard detector suitable for gas chromatographic analysis of volatile compounds and may be adapted as described below. The monitor is preferably formatted to determine the concentration of the volatile organic molecules and to output same, e.g., to an apparatus or an operator using the test system. Output to the operator is preferably registered visually and is sometimes referred to herein as a "display" or similar term.

The detector is specifically referred to herein as a "monitor" when it is used to detect respiratory gas that is not fractionated, e.g., by a chromatography system. A preferred monitor in accord with the invention is capable of detecting at least one volatile organic molecule and providing output relating to that volatile organic molecule in unfractioned respiratory gas such as human breath. The detector preferably detects and provides output relating to the volatile organic molecules in fractioned gas, e.g., human breath that has been fractioned by the chromatography system.

Position of the monitor in the test system and especially with respect to the chamber will vary depending on several parameters including intended use. However, it is generally preferred that the position be optimized to detect the volatile organic molecules. For example, in a preferred embodiment, the monitor is positioned inside the chamber along or near flow lines of the respiratory gas. In this embodiment, the monitor is suitably configured to provide the output to the apparatus or the operator as needed.

In another embodiment of the test system, the monitor includes or is interfaced with a computational system such as those described below. In a particular embodiment, the computational system is formatted to correlate the concentration of at least one of the detected organic molecules (test value) to a pre-determined (control) value and to output results of the correlation. The control value is indicative of normal hepatic function in the mammal and is referenced by the test system in many embodiments of the invention. However, in other embodiments, the computational system will correlate the test value to an analytical value that is indicative of the presence and preferably the stage of a specific hepatic disorder in the mammal. In still other embodiments, the computational system will correlate the test value to the control and analytical values independently or at the same time. It is generally preferred that the monitor be capable of providing real-time display, e.g., by indicating to the operator in a digital or other suitable format if or when the test value varies significantly from the control value.

In another embodiment, the monitor further includes or is interfaced with a standard carbon dioxide analyzer that preferably corrects (i.e., normalizes) the concentration of at least one of the detected organic molecules to an alveolar concentration of carbon dioxide. In this embodiment, the monitor is preferably further capable of outputting the concentration of one of the detected organic molecules and the alveolar concentration of carbon dioxide, e.g., to another apparatus or to the operator of the test system.

In more particular embodiments of the test system, the computational system includes at least one program and typically one program to achieve the output. Preferably, the program is adapted to perform at least one pre-determined arithmetic manipulation. It will be appreciated by those of skill that at least some or in some cases all of the manipulations can be performed by the operator without significant assistance of the computational system. For example, for some applications, the operator may use, e.g., a standard pocket calculator or other computational device such as a slide rule to perform the manipulations. However, it is generally preferred that the program perform nearly all or all of the arithmetic manipulations particularly in embodiments where real-time analysis or analysis of multiple patient samples is contemplated.

In a more specific embodiment, the arithmetic program includes or consists of computer software that is preferably capable of determining the concentrations of the volatile organic molecules and, in some embodiments, correcting same to the alveolar concentration of carbon dioxide. In this embodiment, the concentration of one of the detected organic molecules can be correlated to the control or the analytical value (or both values) as desired. More specific disclosure relating to suitable software embodiments are provided in the discussion and examples which follow.

Preferred arithmetic programs are capable of conducting at least one parametric test to determine statistical significance between the concentration of at least one of the detected organic molecules and the control or analytical value (or both values). The monitor comprising the arithmetic program can be especially formatted to register as output statistical significance between the concentration of the detected organic molecule and the control or analytical value if desired. For example, in one embodiment, the monitor is adapted to output at least one of the following parameters to the operator: the concentration of one of the volatile organic molecules detected by the monitor; the predetermined control value, analytical value, or both; and results of the parametric test. If desired, the output may further include the alveolar concentration of carbon dioxide determined by the analyzer. As discussed, it is generally preferred to provide the output in real-time although for some applications delayed or stored output may be preferred.

In another embodiment, the invention features a test system that includes at least one and preferably all of the following components:

a) a gas collection apparatus for receiving respiratory gas and preferably breath from the mammal and to output volatile organic molecules in the gas, b) a chromatography system for receiving the volatile organic molecules from the apparatus and to detect volatile organic molecules comprising at least one of hydrocarbon or organosulfur molecule; and c) a computational system adapted to process output from the chromatography system, wherein the computational system preferably comprises at least one program and preferably one program adapted to perform at least the following steps:

i) determine concentration of at least one of the volatile organic molecules detected by the chromatography system, ii) correlate the concentration of at least one of the detected organic molecules to the pre-determined control value, the analytical value or both; and iii) output results, e.g., to an apparatus or to an operator as a display.

In one embodiment, the gas collection apparatus of the test system has a sampling volume and particularly a concentration capacity of less than about 25 liters. Preferably, the apparatus is adapted to collect breath samples from the human patient and can be used for single use or multiple use gas output to the chromatography system.

In a particular embodiment, the chromatography system preferably includes a pair of gas chromatographs each individually comprising a standard detector for detecting the hydrocarbon or sulfur. That is, the chromatography system more particularly includes a pair of detectors for detecting the hydrocarbon or organosulfur molecules. It is generally preferred that the pair of gas chromatographs be configured together in the test system, although in some cases it may be useful to remove one of the gas chromatographs from the test system to perform a separate analysis. In this embodiment, the test system employs a computational system as described above.

More preferred test systems in accord with the invention detect volatile organosulfur compounds. In additionally preferred embodiments, the test systems are adapted to detect and preferably stage a specific hepatic disorder such as a hepatocellular injury or a biliary tract disorder.

The present test systems provide several important advantages. For example, preferred use of the test systems provides a useful and dynamic evaluation of hepatic function in real-time. The test systems correlate concentration of at least one of the detected volatile organic molecules to the pre-determined control or analytical value (or both). Statistically significant test results are determined and then displayed to the operator to facilitate evaluation of the presence and preferably the stage of hepatic dysfunction in the patient.

The test systems of the present invention are highly flexible and can be used to correlate the concentration of a single detected organic molecule to single control or analytical value or to multiple values at the same time or at different times. For example, in one embodiment, a first analytical value can be indicative of an early stage of a specific hepatic disorder and one or more additional analytical values can be indicative of more advanced severity (e.g., mid- or late stage) of that same disorder. Alternatively, each analytical value can be indicative of distinct hepatic disorders. If desired, the control values, the analytical values or both can be tailored to a particular patient or even to a specific group of patients to provide an opportunity for significant and highly personalized health care.

Additionally, the present test systems enhance the statistical significance of test results by reference to the pre-determined values. More specifically, it has been found that when raw test data is logarithmically transformed according to the preferred manipulations described below, the resulting transformed data is more reliable and exhibits a more normal distribution (ie. less statistical variance). The present invention takes advantage of this discovery by using control and analytical values based on statistically relevant data. As discussed, in preferred embodiments, the computational system performs at least one parametric test using such data, thereby further enhancing reliability and statistical significance of the output.

The present test systems are particularly useful for providing "early warning" relating to the onset (or recurrence) of a specific hepatic disorder. Significantly, by reference to the pre-determined values, detection and preferably staging of more advanced disease states is possible. Thus, the present test systems are especially appropriate for use with subjects that are predisposed (or suspected of being predisposed) to liver damage arising from deleterious genetic or environmental influences.

Additionally, the present test systems are well-suited as research tools. For example, the test systems can be used to assay specific biomarkers discussed herein or they can be used to identify new biomarkers for detecting and preferably staging a desired hepatic disorder. Importantly, preferred use of the present test systems will extend understanding of the molecular composition of respiratory gas and especially human breath in normal subjects or those afflicted with hepatic disease.

In another aspect, the present invention features methods for detecting and preferably staging a hepatic disorder in a mammal such as a human patient. In one embodiment, the method includes at least one and preferably all of the following steps:

a) collecting respiratory gas from the mammal, b) determining the concentration of at least one volatile organic molecule in the respiratory gas; and c) correlating the concentration of the volatile organic molecule to presence and stage of the hepatic disorder in the mammal.

In one embodiment of the method, the respiratory gas is received into a chamber that is configured to receive the gas and preferably breath from the mammal. In a more specific embodiment, a monitor is used for detecting at least one volatile organic molecule in the respiratory gas and for outputting the concentration of at least one of the detected organic molecules preferably in real-time.

In another embodiment of the method, the respiratory gas is collected into a gas collection apparatus that is preferably adapted to concentrate volatile organic molecules therein. In a more particular embodiment, the gas collection apparatus is heated to release the molecules therefrom, and the released molecules are separated on a chromatography system capable of detecting at least one of hydrocarbon or an organosulfur molecule. In this embodiment, the chromatography system preferably detects at least one of the volatile organic molecules.

In a particular embodiment, the gas collection apparatus used in the method has a sampling volume of less than about 25 liters. Preferably, the apparatus is especially adapted to collect a breath sample from the human patient. In another particular embodiment, the chromatography system employed in the method preferably includes a pair of gas chromatographs each individually comprising a standard detector for detecting the hydrocarbon or organosulfur molecule. It is generally preferred that the pair of gas chromatographs be configured together although in some cases it may be useful to separate each of the gas chromatographs from the other as noted previously.

In another particular embodiment, the correlation step further comprises correcting the concentration of the organic molecule to an alveolar concentration of carbon dioxide respired by the mammal. As discussed, the correlation step can be performed by one or a combination of different strategies. For example, in one approach, the computational system can be employed to perform arithmetic manipulations sufficient to correct the concentration. The alveolar carbon dioxide exhaled by the mammal can be collected and measured as part of the present methods. Alternatively, the alveolar carbon dioxide can be measured apart from the method, e.g., by independently testing the respiratory gas sample.

In a more particular embodiment, the correlating step further comprises determining concentrations of the detected organic molecules and comparing the concentration of at least one of the molecules to the pre-determined control value, the analytical value, or both. Preferably, the correlating step is achieved by using a suitable computer system such as those disclosed herein.

In another particular embodiment, the correlating step of the method further comprises performing a parametric test between the concentration of the detected organic molecule and the predetermined control or analytical value. In a more specific embodiment, the detected organic molecule is at least one of a volatile hydrocarbon or a volatile organosulfur molecule such as those specified below.

It will be appreciated that in embodiments of the invention in which the alveolar carbon dioxide concentration for a given mammal is known (e.g., a human patient), practice of the invention need not include measurement of the alveolar carbon dioxide in a respiratory gas sample taken from that mammal.

In another embodiment, the invention features a method for detecting and staging a hepatic disorder in a mammal and preferably a human patient. The method includes at least one and preferably all of the following steps:

a) collecting respiratory gas and preferably breath from the mammal into a gas collection apparatus adapted to concentrate volatile organic molecules therein, b) separating the released molecules on a first gas chromatograph comprising a first detector capable of detecting hydrocarbon, c) detecting ethane in the released molecules, d) separating the released molecules on a second gas chromatograph comprising a second detector capable of detecting organosulfur molecules, e) detecting at least one of carbonyl sulfide or dimethyl sulfide in the released molecules; and f) correlating concentration of at least one of ethane, carbonyl sulfide or dimethyl sulfide to the presence and stage of the hepatic system disorder in the mammal.

In a particular embodiment, the gas collection apparatus used in the method has a sampling volume of less than about 25 liters. Preferably, the gas collection apparatus is heated to release the molecules and is especially adapted to collect a breath sample from the human patient. In a more particular embodiment, the correlation step further comprises correcting the concentration of the carbonyl sulfide or dimethyl sulfide to an alveolar concentration of carbon dioxide respired by the mammal. The correlation step can be performed by one or a combination of different methods as discussed above and in the following examples. Preferably, the correlating step further comprises determining concentrations of the carbonyl sulfide or dimethyl sulfide and comparing the concentration of at least one of the molecules to the pre-determined control value, the analytical value, or both.

In a more specific embodiment, the correlating step further comprises performing a parametric test between the concentration of the carbonyl sulfide, or dimethyl sulfide in the respiratory gas sample obtained from the mammal and the pre-determined control value, the analytical value, or both. If desired, the parametric test may be performed with other reference molecules including standard volatile organic molecules as needed.

The order in which the first and second chromatographs are used in the method is not important so long as the presence and stage of the hepatic disorder can be detected in the mammal.

In another embodiment, the present invention features methods for detecting a hepatic disorder in a mammal and especially a human patient. In a particular embodiment, the method includes at least one and preferably all of the following steps:

a) collecting respiratory gas from the mammal, b) determining concentration of carbonyl sulfide in the respiratory gas; and c) correlating the concentration of carbonyl sulfide to the presence of the hepatic disorder in the mammal.

In one embodiment, the respiratory gas is collected into a gas collection apparatus that is adapted to concentrate volatile organic molecules therein. Preferably, the respiratory gas is breath from the mammal. In a more particular embodiment, the gas collection apparatus is heated to release the molecules therefrom and the released molecules are separated on a chromatography system capable of detecting at least one of hydrocarbon or sulfur. Preferably, the chromatography system is capable of detecting the carbonyl sulfide in the released molecules.

In another particular embodiment, the gas collection apparatus used in the method has a sampling volume of less than about 25 liters. Preferably, the apparatus is especially adapted to collect a breath sample from the human patient. In a more particular embodiment of the method, the chromatographic system comprises a pair of gas chromatographs each individually comprising a detector for detecting hydrocarbon or organosulfur molecules.

In another particular embodiment, the correlation step of the method further comprises correcting the concentration of the ethane or carbonyl sulfide to an alveolar concentration of carbon dioxide respired by the mammal. The correlation step can be performed by one or a combination of different methods mentioned previously and in the discussion and examples that follow. For example, the correlating step preferably further includes determining concentrations of the carbonyl sulfide and comparing the concentration of at least one of the molecules to the pre-determined control value, the analytical value (or both) as described below.

In a specific embodiment, the correlating step of the method further comprises performing a parametric test between the concentration of the carbonyl sulfide in the respiratory gas obtained from the mammal and the predetermined control value, the analytical value (or both).

In another embodiment, the present invention features methods for detecting a hepatocelluar injury or a biliary tract disorder in a mammal and particularly a human patient. In one embodiment, the method includes at least one and preferably all of the following steps:
  a) collecting respiratory gas from the mammal,
  b) determining concentration of at least one of ethane, carbonyl sulfide, or dimethyl sulfide in the respiratory gas; and
  c) correlating the concentration of at least one of the ethane, carbonyl sulfide or dimethyl sulfide to the presence of the hepatocellular injury or the biliary tract disorder in the mammal.

In one embodiment, the respiratory gas is collected into the gas collection apparatus that is adapted to concentrate volatile organic molecules therein. Preferably, the gas is breath from the mammal. In a more particular embodiment, the gas collection apparatus is heated to release the molecules therefrom and the released molecules are separated on a gas chromatographic system capable of detecting at least one of hydrocarbon or an organosulfur molecule. Preferably, the chromatographic system is capable of detecting at least one of ethane, carbonyl sulfide or dimethyl sulfide in the released molecules.

In another particular embodiment, the gas collection apparatus used in the method has a sampling volume of less than about 25 liters. Preferably, the apparatus is especially adapted to collect a breath sample from the human patient. In a more particular embodiment of the method, the gas chromatographic system comprises a pair of gas chromatographs each individually comprising a detector for detecting the hydrocarbon or an organosulfur molecule. In a more particular embodiment, the correlation step of the method further comprises correcting the concentration of the ethane, carbonyl sulfide or dimethyl sulfide to an alveolar concentration of carbon dioxide exhaled by the mammal. In a specific embodiment, the correlating step of the method further comprises performing a parametric test between the concentration of the detected ethane, dimethyl sulfide, or carbonyl sulfide in the respiratory gas and the predetermined control value, the analytical value (or both).

In another embodiment, the method further comprises staging the hepatocellular injury or biliary tract disorder in the mammal as described below.

Further provided by the invention is a test system that includes the computational system discussed above. In this example of the invention, the computational system is preferably capable of receiving input from the monitor or detector and outputting data, preferably in real-time, to the system user.

BRIEF DESCRIPTION OF THE DRAWINGS

FIGS. 1A and 1B are drawings showing preferred examples of the present test systems as block diagrams.

DETAILED DESCRIPTION OF THE INVENTION

Figure 1C:
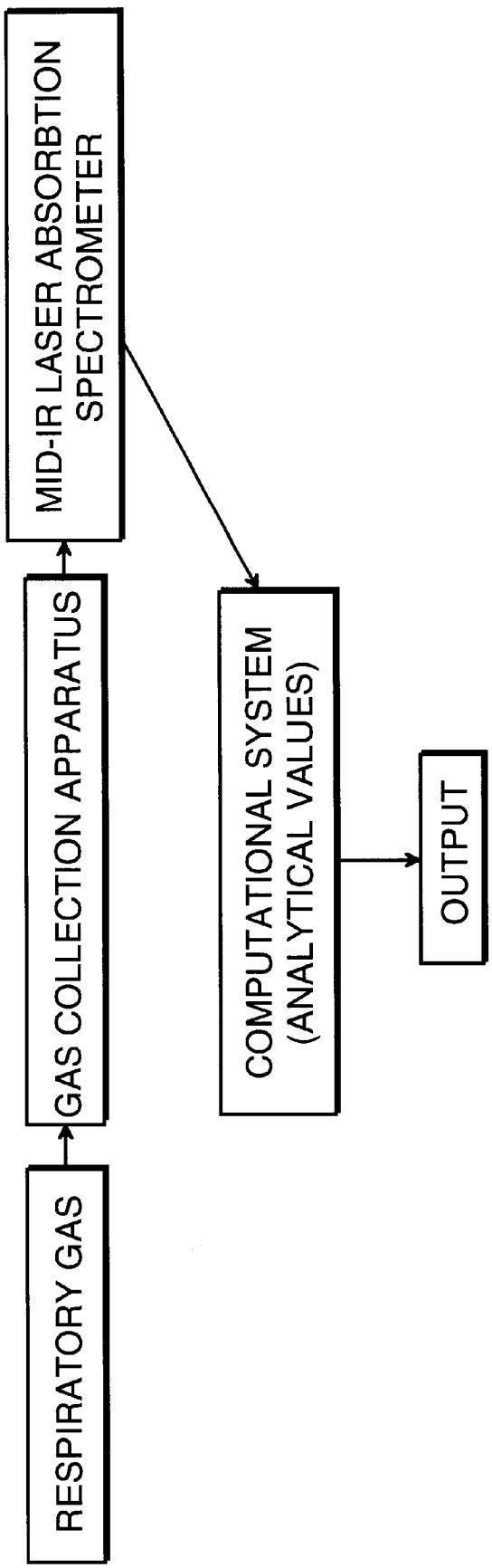
FIG. 1C is a drawing showing another preferred example of the present test system. Shown as a block diagram is a "mid-IR laser absorption spectrometer" comprising a lead-salt tunable diode laser (TDL) linked to a Harriott multi-pass gas cell as described in the text.

As discussed, the present invention relates to test systems and methods for detecting and preferably staging hepatic disorders in a mammal such as a human patient. In particular, the invention can be used to detect, classify and stage a wide spectrum of hepatic disorders. Illustrative hepatic disorders include chronic liver failure such as those associated with substance abuse, genetic deficiency, viral infection, exposure to poison, or an autoimmune response. The present invention is also useful for a wide spectrum of applications, including evaluation of patients that have received certain donated tissue and particularly an organ such as a liver transplant.

By the term "hepatic disorder" or related phrase is meant a mammalian and preferably a human liver disease or condition associated with hepatocellular injury or a biliary tract disorder. Preferred hepatocellular injuries include alcoholic cirrhosis, $\alpha$-1 antitypsin deficiency, autoimmune cirrhosis, cryptogenic cirrhosis, fulminant hepatitis, hepatitis B and C, and steatohepatitis. Preferred examples of biliary tract disorders include cystic fibrosis, primary biliary cirrhosis, sclerosing cholangitis and biliary obstruction. See, e.g., Wiesner, R. H, Current Indications, Contra Indications and Timing for Liver Transplantation (1996), in *Transplantation of the Liver*, Saunders (publ.); Busuttil, R. W. and Klintmalm, G. B. (eds.) Chapter 6, e.g., Tables 6–3 and 6–5 as well as FIGS. 6–11; Klein, A. W., (1998) Partial Hypertension: The Role of Liver Transplantation, Musby (publ.) in *Current Surgical Therapy* $6^{th}$ Ed. Cameron, J. (ed) for more specific disclosure relating to these disorders.

As discussed, the present invention features test systems for detecting and preferably staging a hepatic disorder in a mammal such as a human patient. The term "test system" as used herein means a configuration of components that are designed to collect and analyze volatile organic molecules preferably to detect the presence and preferably the stage or the hepatic disorder. The components can be organized as desired provided that the test system performs the function for which it was intended. Preferred use of the invention involves analysis of respiratory gas from a mammal and especially a human patient. By the term "respiratory gas" is meant gas exhaled from the lungs including gas passing through an orifice such as the mouth or nose. Breath from the human patient is a preferred example of respiratory gas.

In one embodiment of the present invention, the test system includes a chamber and a monitor. The chamber typically includes an intake port for receiving the respiratory gas, usually from a patient's mouth or nose, and an outlet port for outputting the respiratory gas, and an orifice for receiving the monitor or a detecting portion of that monitor. Illustrative chambers for use in accord with the invention can be purchased, e.g., from Pryon Corp.

As discussed, the monitor of the test system can be provided in one or a combination of different formats. For example, in one embodiment, the monitor is a standard detector and particularly a detector such as those compatible with a chromatography system and especially a gas chromatograph (GC). The detector is preferably formated to detect at least one volatile organic molecule and to provide output relating to the detection e.g., to an operator in real-time. The detector can be positioned with respect to the chamber in several ways including inside the chamber, partially inside the chamber or adjacent to the chamber, e.g., near the outlet port. In a more specific embodiment, the monitor is a flame detector that is preferably positioned inside the chamber to analyze respiratory gas therein. In a more particular embodiment, the flame detector is equipped with a baffling system such as a standard split-stream device to reduce or control flow into the detector. Nearly any GC flame detector is suitable for use with the invention including those designed to detect organosulfur molecules. An especially preferred detector is a sulfur-selective flame detector as provided in the examples below. It will be appreciated that use of detectors to detect volatile organic molecules including organosulfur compounds is well-known in the field.

Several other monitors can be used in accord with the present invention. Illustrative monitors include those based on chemiluminescence and capable of detecting sulfur compounds (Sievers, Corp). Further, standard infra-red (IR) detectors can be used as suitable monitors, such as those available from Pryon Corp. In this embodiment, it is preferred to configure the chamber with a suitable IR source to excite the gas energetically. Additional monitors include those formatted for Raman scattering or mass spectrometer applications. See e.g., Tauchez, J. et al. (1997) *Rapid Comm. in Mass Spectromety* 11: 1230.

Additionally monitors include those adapted for detecting and preferably measuring at least one gas and particularly at least one of the following molecules: NO, CO, $CO_2$, $N_2O$, $NH_3$, $C_2H_6$, and $H_2O_2$. More preferred is a monitor adapted for detecting and measuring all of the molecules in a human breath sample. More particularly preferred is a monitor comprising or consisting of an infra-red (IR) sensitive spectrometer, especially those spectrometers well-suited for performing non-dispersive IR. Illustrative monitors are available from the Pryon Corp. as well as other commercial vendors.

More preferred monitors for use with this invention include or consist of the IR sensitive spectrometer linked to compatible multiple-pass gas cell. A more particularly preferred spectrometer includes a laser such as a lead-salt tunable diode laser (TDL) made from columns IVA and VIA of the periodic table and capable of emission in the range of about 3 to about 20 $\mu$M. Still more preferred is a mid-IR sensitive laser spectrometer that includes the TDL optically linked to a Harriot multi-pass gas cell. Especially preferred monitors also include recognized system components such as one or more beam splitters, mirrors, vacuum, photodiode detector, and low temperature bath.

A particularly preferred monitor for use with this invention includes or consists of a mid-IR laser absorption spectrometer as described by Namjou, K. et al. See Namjou, K. et al. (1999) in *Application of Tunable Diode and Other Infrared Sources for Atmospheric Studies and Industrial Processing Monitoring II, SPIE Annual Meeting,* Denver, Colo. (July 18–23) for more detailed disclosure relating to making and using this monitor.

See also McManus, P. L. et al. (1995) *Applied Optics* 34: 3336; Kouznetsov, A. I. et al. (1998) in Detection of Endogenous NO and CO in Breath Using TDL: Applications for Human Physiology and Clinical Diagnostics, *Proc. $2^{nd}$ International Conf. on Tunable Diode Laser Spectroscopy,* 43, Moscow, Russia; Lee, P. S. et al. (1998) IEEE Transactions on Biomedical Engineering 38: 966 (1991); and Mitsui, T. et al. (1998) *Sci. Total Environ.* 224: 177 for disclosure relating to making and using the mid-IR laser absorption spectrometer. The monitor described by Namjou, K. et al. supra, is fully compatible with the present invention and can be used to facilitate effective detection and measurement a wide spectrum of useful biomarkers.

Accordingly, in the embodiment of the invention shown schematically in FIG. 1B, the "chromatography system" can be augmented or replaced with at least one mass spectrometer, preferably an IR sensitive spectrometer as described above. In a preferred embodiment, the "chromatography system" is replaced with the mid-IR laser absorption spectrometer disclosed by Namjou, K. et al., supra. In this embodiment, the mid-IR laser absorption spectrometer is preferably equipped with a Fourier transform IR spectrometer or other suitably IR sensitive spectrometer as described by Namjou, K. et al, supra.

In embodiments of the invention in which the "chromatography system" shown schematically in FIG. 1B is augmented with the mass spectrometer, the system can be, e.g., a chromatography-mass spectrometer implementation such as a standard GC-mass spectrometer (ie. GC-MS) or a related device. See U.S. Pat. Nos. 5,525,799, 3,641,339; and references cited therein for more disclosure relating to GC-MS.

In more specific embodiments of this invention, the monitor is interfaced with a suitable computational system that is preferably adapted to analyze detected organic molecules and to provide the output. An illustrative computational system is as follows.

For example, it is generally preferred that the computational system include at least one mini-computer and typically one mini-computer. Preferably, the mini-computer is adapted to perform the arithmetic program and is interfaced (directly or indirectly) with another apparatus such as the chromatography system discussed below. A variety of suitable mini-computers are commercially available and include those with a CPU system, a display terminal, and associated input and output devices comprising a keyboard and related control units. Memory and CPU requirements will vary depending on several parameters such as the number of test samples to be run and the amount of data, if any, to be stored. More particularly preferred mini-computers are fully compatible with the software programs discussed below.

If desired, the computational system can be part of the monitor, e.g., as a computer chip, to provide desired functions.

Suitable computational systems in accord with the invention can be run in a variety of conventional formats. For example, the computational system can be run on analog or digital computer systems. Software implementing the system may be written in a high level language such as Fortran, C or C++ and run on the mini-computer or CPU. The software may be a stand-alone executable, a functional library an add-on to another application, or embedded in a specific purpose apparatus. The present computational system may also be implemented using a high-level development or mathematical system such as spreadsheet or symbolic mathematical software. Specific data used and/or output by the present test systems may be stored in any form such as a database including relational and object-oriented databases stored on any apparatus including read-only memory (ROM) magnetic disk, CD Rom and erasable magnetic disks. The computational system may also be implemented in hardware, firmware, including special purpose designed integrated circuits (IC) such as ASICs (application specific integrated circuits), programmable logic arrays (PLAs), and gate arrays including field-programmable gate arrays (FPGAs).

A more preferred computational system is adapted to use software such as Excel (Microsoft Corp. Richmond, Wash.). Additionally preferred software includes a suitable statistics package, e.g., STATA (STATA Corp. College Station, Tex.). The statistics package can perform at least one and preferably all of the following parametric tests: analysis of variance, student's T-test, comparison of means (Bonferroni and Scheffe tests), linear regression, multiple regression, logistic regression analyses. More preferred software packages can also perform certain non-parametric tests as needed (Wilcoxin and Kruskal-Willis).

As discussed, the computational system can perform one or a combination of different functions. For example, in one embodiment, the computational system is adapted to determine the concentrations of at least one of the volatile organic molecules detected by the chromatography system. The concentration determination is typically facilitated by standard means, e.g., analysis and comparison with standard volatile compounds such as those specified in the examples below. By the term "standard volatile compound", or similar term, is meant a volatile organic compound having a known formula and concentration. If desired, detection of the standard volatile compounds can be conducted in association with the computational system. Alternatively, the concentration of the standard volatile compounds can be determined apart from the test system. See Examples 1 and 2 for more specific disclosure relating to determining the concentration of volatile organic molecules.

As a specific illustration, in some instances it will be desirable to construct a standard curve of a particular volatile organic molecule of interest and to determine the concentration of that molecule by correlating a detected peak or signal to the curve. As will be readily apparent, the standard curve can be made using nearly any test system described herein including those that comprise a monitor or detector.

In a more preferred embodiment, the concentration of a detected volatile organic molecule is corrected (i.e. normalized) to an alveolar concentration of carbon dioxide exhaled by the mammal. If desired, the alveolar carbon dioxide can be collected and measured as part of a test system described herein. Alternatively, the alveolar carbon dioxide can be measured apart from the test system, e.g., by testing the respiratory gas prior to, during or after analysis using a suitable carbon dioxide analyzer. It will be appreciated that in embodiments in which the alveolar carbon dioxide concentration for a given mammal is known, such as in a particular human patient, the correction can be conducted by the computational system, usually automatically, and usually without measuring the alveolar carbon dioxide in the respiratory gas. Examples 2–3 below provide more specific methods for correcting concentrations of specific volatile organic molecules to an alveolar carbon dioxide level.

In more preferred embodiments, the concentration of carbon dioxide exhaled by the mammal and especially a human patient is greater than about 15 Torr and more particularly from between about 20 to 50 Torr of carbon dioxide and more preferably about 40 Torr.

It will be apparent from the foregoing that in embodiments of this invention in which the computational system is capable of monitoring carbon dioxide in a breath sample or if $CO_2$ levels for a particular subject are already understood, the $CO_2$ analyzer depicted in FIG. 1B may not always be needed.

As discussed, in some embodiments of the present test systems, at least one pre-determined analytical value is referenced in the computational system. In other embodiments, however, at least one of the pre-determined analytical values is referenced in the monitor. The analytical value is the mean concentration of a specific volatile organic molecule in respiratory gas obtained from a mammal (typically a human patient) afflicted with the hepatic disorder. The analytical value is preferably determined by analyzing a statistically significant plurality of respiratory gas samples collected independently from afflicted and non-afflicted (normal) mammals. Specific methods for determining analytical values are discussed as follows.

For example, in one approach, the pre-determined analytical value is determined by first producing the control value. The control value is the mean concentration of a specific volatile organic molecule in respiratory gas obtained from a mammal (typically a human patient) that is not afflicted with the hepatic disorder. If desired, the respiratory gas may be collected from a statistically significant plurality of normal mammals. A preferred method for obtaining the control value is as follows: raw test data is obtained from chromatographic analysis of a statistically significant plurality of respiratory gas samples obtained from normal mammals. The raw test data is then logarithmically transformed. The logarithmic transformation is preferably sufficient to normalize the raw control data and produce the "control" value. Statistical significance between the control value and the analytical value is confirmed by performing at least one and usually one parametric test between the control value and the analytical value. Results of the parametric test are statistically significant if it has a p value of from between about $10^{-5}$ to 0.05. More specific methods for determining control values are shown in the following examples.

Specific control values for ethane, dimethyl sulfide and carbonyl sulfide (normal human breath) can be found, e.g., in Tables 2–5 and the examples that follow.

The pre-determined analytical value can also be determined in a number of ways. For example, in one approach, the value is determined by logarithmically transforming raw test data obtained from chromatographic analysis of a statistically significant plurality of respiratory gas samples obtained from mammals that manifest the presence and preferably a specific stage of the hepatic disorder. Preferably, the mammal is a human patient and the transformation is sufficient to normalize the raw test data and produce the analytical value. Also preferably, at least one and usually one parametric test is conducted between the control value and the analytical value., i.e., the parametric test, which produces a p value of from between about $10^{-5}$ to 0.05. The analytical and control values are preferably presented in moles/L although other units may be useful for some applications. Analytical values that exhibit a statistically significant difference from the control values are specifically preferred.

Specific analytical values for ethane, carbonyl sulfide and dimethyl sulfide (breath from human patients) are disclosed in the examples and Tables 2–5.

The mean concentration of the volatile organic molecule in respiratory gas can be determined by one or a combination of strategies including gas chromatography and mass spectrometry. For example, the mean concentration can be more particularly determined by reference to a standard curve made by employing known amounts of a standard volatile organic molecule.

In a more specific embodiment, the test system includes: 1) a gas collection apparatus, 2) a chromatography system and 3) a computational system. In this embodiment, the gas collection apparatus can be provided in variety of suitable forms. For example, in one particular embodiment, the gas collection apparatus includes an intake port for receiving the respiratory gas and an outlet port for outputting the volatile organic molecules in the gas. The outlet port can be connected directly or indirectly to the chromatography system as needed. See e.g., Tangerman et al., supra, Husamura, M., J. A., supra, Phillips et al., supra, Risby, et al, supra, and Kazui et al., supra, for examples of suitable gas collection apparatuses.

A preferred gas collection apparatus includes an operably linked two-way non-breathing valve (NRV), respiratory tubing and a collection bag that is preferably air-tight. In a more preferred embodiment, at least one and preferably two biological filters and a disposable mouthpiece are used in-line on the mouthpart of the NRV. More specific disclosure relating the gas collection apparatus can be found e.g., in Arterbery et al., *Free Radic Biol. Med.*, (1994); 17: 569; Miller et al., *Circul*, (1997) 96: 1097; and Schwartz et al., *J. Pediat. Gastroent. & Nutrit.*, (1997); 24: 68. See the examples which follow.

A preferred gas collection apparatus is capable of concentrating from between about 0.01 liters to 20 liters and more preferably from between about 0.02 liters to 1 liter or less of respiratory gas. A more preferred gas collection apparatus is capable of concentrating from between about 0.02 liters to 0.5 liters and more preferably from between 0.03 liters to 0.3 liters. See Examples 1–2 below.

Preferred operation of the gas collection apparatus involves taking a respiratory gas sample from a resting patient, e.g., inclined or seated, and using a pre-determined ventilation pattern for that patient. In more preferred embodiments, the sample is taken from the patient over about a minute. See Example 1 below.

The chromatography system of the test system can be provided in one or a combination of suitable forms. For example, in a preferred embodiment, the chromatography system includes or consists of a conventional gas chromatography (GC) system that is able to detect volatile organic compounds and particularly specific hydrocarbons and organosulfur compounds. In a preferred embodiment, the GC includes a pair of standard gas chromatographs each individually comprising a conventional GC detector for detecting and preferably quantitating hydrocarbon or organosulfur molecules in the respiratory gas sample. As discussed above, the GC system can consist of a pair of gas chromatographs configured together. Alternatively, the GC system may be separated into multiple GC systems including two gas chromatographs such as when it is useful to facilitate analysis by multiple clinicians or laboratories.

In preferred embodiments, the GC detector is a standard flame ionization (non-selective) detector or a sulfur-selective flame photometric detector. In use, the detectors are preferably optimized for the detection of hydrocarbons or organosulfur molecules, respectively. See e.g., Chen et al., supra, Kaji et al., supra, Tangerman et al., supra, Hisamura, M., supra, Risby et al., supra and Kazui et al., supra, for additional disclosure relating to preferred gas chromatographs. An especially preferred gas chromatograph is compatible with a conventional capillary column. See Example 3 below.

If desired, the chromatography system, and particularly the GC system, may be interfaced directly or indirectly with a suitable mass spectrometer and particularly an electron impact mass spectrometer. For example, the mass spectrometer can be used to identify volatile organic molecules in the respiratory gas. See Example 3 below.

Preferred use of the present test systems involves receiving a sample of respiratory gas from a human patient and detecting at least one volatile organic molecule, e.g., a specific organosulfur molecules in the gas. The detection can be performed by the monitor or chromatography system as desired. The test systems preferably further include a computational system for determining (ie. computing) the concentration of the detected organic molecule, comparing the concentration to a pre-determined control value, analytical value (or both) and outputting statistically significant comparison results to another apparatus or to an operator, e.g., as a real-time digital display. See Tables 2–5 below for examples comparing control and test results.

FIGS. 1A and 1B provide examples of specifically preferred test systems in block diagram format.

For example, FIG. 1A shows a test system in which respiratory gas, e.g., from a human patient, is collected and analyzed by a suitable monitor. In a particular embodiment, the monitor includes a computational system for detecting at least one organosulfur molecule in the gas, determining the concentration of the detected organosulfur molecule, correlating the concentration to a control value indicative of normal hepatic function, and outputting statistically significant results to an operator. In a specific embodiment, the output is formated as a signal which can be visually registered, e.g., a light or audio source, which is preferably engaged when the determined concentration varies from control value by a statistically significant amount. As discussed, it is preferred to determine statistical significance by performing a parametric test as described herein. Alternatively, the output can be stored by the monitor for later analysis.

FIG. 1B shows an additional embodiment of the present test systems. In this illustration, a respiratory gas sample is received from a mammal and preferably a human patient. The gas is preferably collected and concentrated in the gas collection apparatus and outputed to the chromatography system for fractionation of volatile organic molecules therein. In preferred embodiments, the chromatography system comprises a pair of gas chromatographs including suitable detectors for detecting volatile organic molecules including hydrocarbon and organosulfur compounds. In this embodiment, the chromatography system is interfaced directly or indirectly with a suitable computational system capable of correlating the concentration of the detected organic molecules to the analytical value, the control value, or both. In a specific embodiment, the output is formated as a signal which can be visually registered, e.g., a light or audio source, which is operative when the determined concentration varies from control value or the analytical value (or both) by a statistically significant amount as determined by a parametric test described herein. Alternatively, the output can be stored by the computational system for later analysis.

By the term "correlating" as it is used herein to describe relationship between a detected volatile organic molecule and a pre-determined control or analytical value is meant comparison between the detected molecule and the pre-determined control or analytical value. The comparison can be performed by any method described herein including use of a computational system. Results of the comparison are evaluated for statistical significance by a suitable parametric test. In many instances, statistically significant comparison results are provided as output by the test system.

See Examples 1–3 below and FIGS. 4–6 for specific examples of detecting the presence and stage of a hepatocellular injury or bile duct injury in a patient.

As discussed, preferred use of the present invention involves the detection and preferably staging of a human hepatic disorder. By the term "stage" or like term as it is used in reference to a hepatic disorder is meant a clinical assessment of the stage (severity) or progression of that specific disorder in the mammal. For example, as the term is used and understood in the field, it is meant to denote whether a specific patient has the hepatic disorder (none) or whether the severity or progression of that disorder has advanced to an early-, mid- or late-stage for that patient. See, e.g., Wiesner, R. H., supra and Klein A. W. supra for more specific disclosure relating to staging bile duct injury and hepatocellular injury.

As discussed, the present invention also features methods for detecting and preferably staging a hepatic disorder in a mammal such as a human patient. As desired, the methods are well-suited for analysis of modest respiratory gas samples such as those provided by children and especially infants, as well as infirm or ill adults. For example, in one embodiment, the methods use a gas collection apparatus that has a preferred sample volume of from between about 0.01 liters to 20 liters and more preferably from between about 0.02 liters to 1 liter or less of respiratory gas. A more preferred gas collection apparatus is capable of concentrating between about 0.02 liters to 0.5 liters and more preferably 0.03 liters to 0.3 liters.

As will be pointed out in the examples that follow, it has been found that use of the gas collection apparatus can be optimized to enhance data collection. For example, in a preferred embodiment, the methods use a gas collection apparatus that includes a gas collection chamber that further includes a suitable polymeric adsorbent such as Tenax TA. See e.g., Tangerman et al., supra, and references cited therein. The method further comprises cooling the chamber from between about −100° C. to −150° C. to concentrate the volatile organic molecules in the adsorbent. In more specific embodiments, the methods further include heating the chamber from between about 100° C. to 200° C. to release the concentrated volatile organic molecules therefrom into the chromatography system. As discussed below, it has been found that most volatile organic molecules analyzed in accord with the invention can be collected with about 100% efficiency using sampling volumes below 200 ml. See Examples 1–3 and FIGS. 4–6.

More preferred use of the methods involves detection of specific volatile hydrocarbons, e.g., ethane; as well as volatile organosulfur molecules such as carbonyl sulfide and dimethyl sulfide. The present methods can be used to detect a variety of hepatic disorders and particularly hepatocellular injury or a biliary tract disorders.

By the term "volatile organic compound" or like term is meant an organic compound, e.g., hydrocarbon, aldehyde, organosulfur compound, ketone or alcohol, each having from between about 1 to 6 carbons and a molecular weight of less than 400 daltons as determined, e.g., by mass spectrometry or gas chromatography. Particular volatile organic compounds include acetone, dimethyl ketone, ethanol, etc. A volatile hydrocarbon or like term means a straight-chain or branched-chain hydrocarbon having between about 1 to 6 carbons such as methane, ethane, ethene, isoprene, etc. An especially preferred volatile hydrocarbon is ethane. A volatile organosulfur molecule or compound or like term means a volatile organic compound that includes sulfur. Particular volatile organosulfur compounds are sulfides having a molecular weight of less than about 400 daltons. Illustrative compounds include carbonyl sulfide, methyl sulfide, dimethyl sulfide, allyl methyl sulfide or cogeners thereof.

All documents mentioned herein are fully incorporated by reference. The following non-limiting examples are illustrative of the invention.

EXAMPLE 1

Breath Collection From Human Patients

Breath samples were collected by means of a two-way non-rebreathing valve (NRV) Hans Rudolf, Kansas City, Mo.) connected by respiratory tubing to gas-tight collection bag (22.4 L, Calibrated Instruments, Inc., Ardsley, N.Y.). Biological filters, preferably two, and a disposable mouthpiece were used in-line on the mouthport of the NRV. This breath collection system has essentially no back pressure and has been used to collect breath from adults and neonates, see Arterbery et al., supra; Miller et al., supra, and Schwarz et al., supra. Breath was collected after one minute of normal breathing. To reduce the potential influence of variations in total and regional alveolar ventilation that may tend to alter the concentration of volatile compounds in breath, breath samples were collected from a seated subject using a pre-determined ventilation pattern. During breath collection, the study subject was asked to breathe with a frequency of approximately 12 breaths/min, and to attempt to maintain tidal volumes that approximate their basal respiratory requirement. Total breath collection over one minute has been found to produce a representative sample, correcting for any differences in individual breaths, and is more reproducible than the collection of end-tidal breath samples.

A. Analysis of carbon dioxide in exhaled breath

Aliquots (20 mL) from the collected samples of exhaled breath were analyzed for their concentrations of carbon dioxide (LB-3 $CO_2$ Beckman Instruments, Fullerton, Calif.). This instrument was calibrated daily using a certified gas standard of carbon dioxide. The concentration of carbon dioxide in the collected breath sample was used in the normalization of breath data and to check the quality of the collected breath sample. Any sample of breath that contained less than 15 Torr of $CO_2$ was not used in any data analysis.

EXAMPLE 2

Concentrating Samples of Room Air and Exhaled Breath

Gaseous samples were concentrated by cryogenic adsorption onto a polymeric adsorbent as follows: a stainless steel wide bore capillary tube (20 cm, 1.65 mm o.d.; 1.19 mm i.d.) packed with 2,6-diphenyl-p-phenylene oxide (60–80 mesh Tenax TA, Alltech Associates, Deerfield, Ill.) was connected to a six-port stainless steel gas sampling valve (1.59 mm inlet, Valco Instruments Co. Inc., Houston, Tex.) in place of the standard gas sampling loop. The length of the adsorbent packing was 10 cm and the packing was retained on either side with plugs of silanized glass wool. The collection tube was submerged in an ethanol/liquid nitrogen slush bath (−119° C.) for six minutes to allow the collection tube and in contents to equilibrate, and then 60 mL of collected gas was drawn through the collection tube using a gas-tight syringe. Cryogenic temperatures increase the adsorption of low boiling point gases onto the surface of the organic adsorbent. After the gas had been sampled, the slush bath was replaced with a specially designed heating block maintained at 160° C. to thermally desorb the collected breath molecules. These molecules were injected immediately onto the gas chromatographic column by rotation of the gas sampling valve. The valve was rotated back to its fill position after 45 seconds and the collection tube was flushed with ultrapure nitrogen to clean it prior to analysis of the next sample. We have determined that the collection tube and its contents reached 160° C. within 30 seconds.

Volatile analyte molecules, such as methane and ethane, are quantitatively adsorbed onto the surface of the polymeric adsorbent at −119° C. without trapping the major components of breath (nitrogen or oxygen). The break-through volumes using the collection tube and the polymeric adsorbent at −119° C. have been investigated and all of the molecules identified to date in breath were found to be collected with approximately 100% efficiency using sampling volumes up to 200 mL. Similarly, thermal desorption temperature at 160° C. has been found to quantitatively desorb the molecules of interest without significant tailing of the solute peaks.

The concentration system has been validated by comparing peak areas for the analyte peaks obtained with regular gas sampling loops and more concentrated gas samples to the peaks areas for the same analyte molecules contained in diluted gas samples using the collection tube, cryogenic concentration and thermal desorption.

EXAMPLE 3

Capillary Gas Chromatographic Analysis of Samples of Room Air and Exhaled Breath A modification of the method developed in our laboratory, Arterbery et al., *Free Radic Biol Med.,* (1994); 17: 569, was used to analyze the concentrated gas samples. The concentrated gas samples were initially analyzed using a wide-bore (60 m, 0.53 mm i.d.) fused silica capillary column wall-coated with dimethyl silicone (7 $\mu$m) using a non-selective flame ionization detector (Varian 3700, Walnut Creek, Calif.). Separation was performed using the following temperature program: hold at 25° C. for ten minutes, 25–200 at 5° C./min, and hold at 200° C. for five minutes. Subsequently, the concentrated gas samples were analyzed using a wide-bore (30 m, 0.53 mm i.d.) fused silica capillary column wall-coated with dimethyl silicone (7 $\mu$m) with a sulfur-selective flame photometric detector (Shimadzu 9A, Shimadzu Corp. Columbia, Md.) using the following temperature program: hold at 25° C. for five minutes, 25–200 at 5° C./min and hold at 200° C. for five minutes. Linear gas (helium) velocities of 25 cm/sec at 25° C. were used for both separation protocols. The analytical methods were calibrated before daily use by injection of standard gas mixtures of sulfur-containing compounds or C1 to C6 straight chain hydrocarbons using the regular gas sampling loops with different volumes. We have demonstrated that the limits of quantification using 30 mL of exhaled breath is <0.1 ppb for the compounds of interest.

The identifications of all compounds were based upon retention volumes and electron impact mass spectral data (Fisons MD 800, Fisons Instruments, Beverly, Mass.). Identical gas chromatographic conditions and columns were used for the confirmational studies by GC-EIMS. Identifications were confirmed by known standards.

Since it is difficult to ensure complete timed collection of exhaled breath the amounts of compounds in the samples are expressed in units of pmol/L corrected to an alveolar concentration of 40 Torr of carbon dioxide and the breath samples were corrected for background levels of the analyte molecules in room air. Only measurable levels of ethane were found in room air.

A. Assay for breath compounds

The coefficient of variation for the determination of levels of breath compounds in replicate samples was found to be 3% (n=100).

B. Data analysis

All data were entered into a spreadsheet (Excel, Microsoft Corporation, Richmond, Wash.) and data analyses were performed using the statistical package, STATA (STATA Corporation, College Station, Tex.). Clinical chemistries and exhaled breath data were entered as continuous variables. Gender, age, race, disease state and staging of liver disease were entered as categorical variables. Analysis of variance, students 1-test, comparisons of means (Bonferroni and Scheffe tests), linear regression, multiple regression, logistic regression analyses and non-parametric tests (Wilcoxin, and Kruskal-Wallis) were used to examine the data.

Table 1 below shows the demographics of the study population. 75% of the study subjects with liver disease presented with alcoholic or cryptogenic cirrhosis, hepatitis C, or sclerosing cholangitis and the remaining 25% presented with an additional 8 liver diseases. This disease distribution is typical of the patient population that attends the clinic. Liver function tests and related blood chemistries (serum urea nitrogen, serum total bilirubin, serum alanine aminotransferase, serum aspartate aminotransferase, serum alkaline phosphatase, serum albumin, and total serum cholesterol) and a clinical assessment of the stage of liver disease (none, early-,mid-or late-stage) were obtained for each study subject. All of these continuous and categorical variables were entered into a spreadsheet. Exhaled breath samples were collected at the same visit when the blood samples were drawn.

TABLE 1

Demographics of study population

|  | Number of study subjects |
|---|---|
| Gender | |
| male | 115 |
| female | 80 |
| Liver Status or Liver Disease | |
| alcoholic cirrhosis | 17 |
| autoimmune cirrhosis | 6 |
| biliary obstruction | 1 |
| cryptogenic cirrhosis | 13 |
| cystic fibrosis | 1 |
| fulminant hepatitis | 1 |
| hepatitis B | 4 |
| hepetitis C | 21 |
| normal | 109 |
| primary biliary cirrhosis | 6 |

TABLE 1-continued

Demographics of study population

| | Number of study subjects |
|---|---|
| sclerosing cholangitis | 12 |
| steatohepatitis | 3 |

Figure 2:
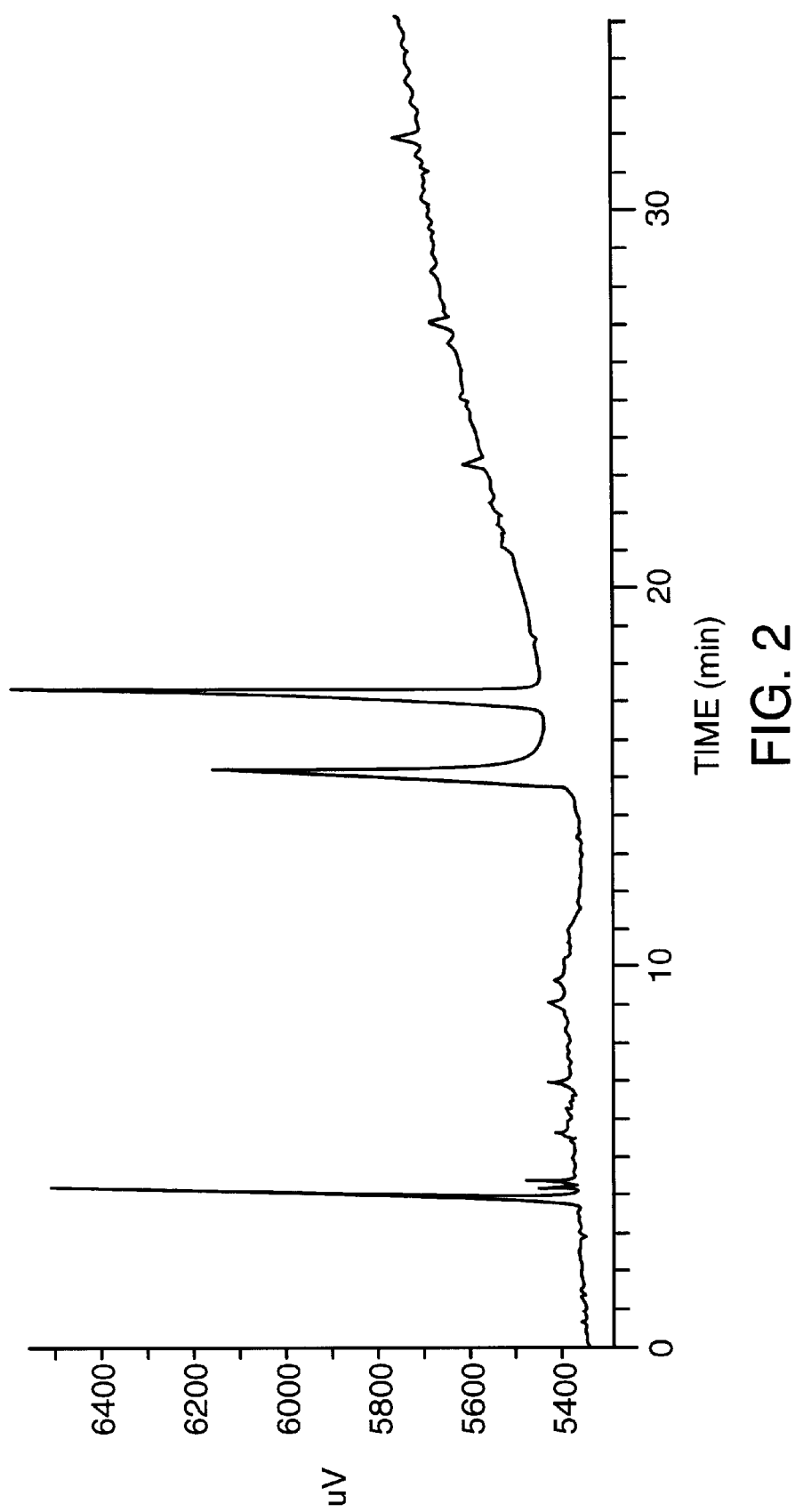
FIG. 2 is a graph showing capillary gas chromatogram of a sample (30 mL) of human breath collected from a study subject with liver disease.
Figure 3:
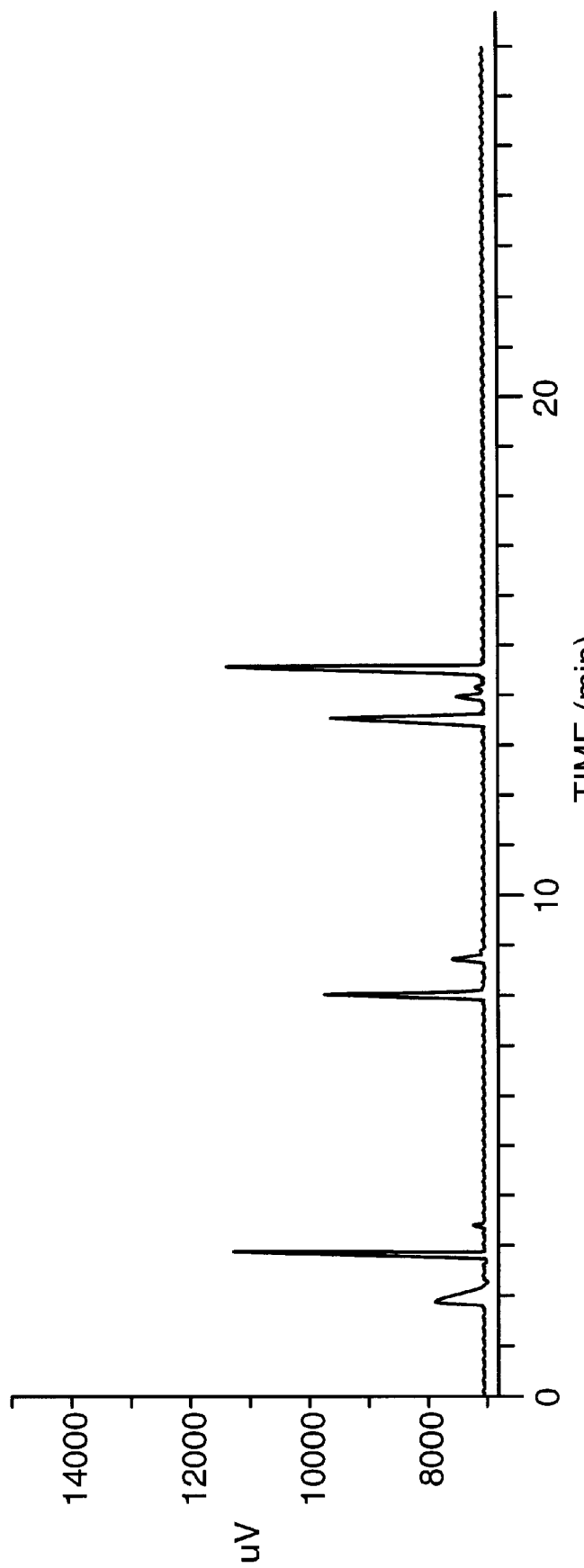
FIG. 3 is a graph showing capillary gas chromatogram of a sample (60 mL) of human breath collected from the same study subject with liver disease.

FIG. 2 shows an example of a capillary gas chromatographic separation of the major constituents found in exhaled breath collected for one of the study subjects with liver disease. This separation was monitored using a flame ionization detector that responds non-selectively to any compound that contains a carbon-hydrogen bond. The major components in exhaled breath in all study subjects were methane, ethene, ethane, dimethyl ketone and isoprene. FIG. 3 shows the separation of the same breath sample using a sulfur-selective detector (flame photometric detector); the major compounds observed were carbonyl sulfide, dimethyl sulfide, dimethyl disulfide, carbon disulfide and the three congeners of allyl methyl sulfide. The sulfur compounds observed in FIG. 3 are not detectable or are below the detection limits for the flame ionization detector. (Note that the two gas chromatograms cannot be superimposed since chromatographic conditions and column lengths are different.) The identifications of these compounds were based upon chromatographic retention data, electron impact mass spectrometric data, and were confirmed with authentic standards. Concentrations of all molecules that have been identified in exhaled breath were determined based upon calibration curves generated with standard gas mixtures. The concentrations of each breath biomarker for the study subjects were entered into the data spreadsheet.

FIG. 2 is more particularly explained as follows: The column effluent was monitored with a flame ionization detector. The identifications and retention times of the peaks were as follows: methane 3.85 min., ethene 4.14 min., ethane 4.31 min., dimethyl ketone 14.76 min., and 2-methyl-1,3-butadiene (sioprene) 16.90 min.

FIG. 3 is explained in more detail as follows: The column effluent was monitored with a flame photometric detector. The identifications and retention times of the peaks were as follows: carbonyl sulfide 2.77 min., methyl sulfide 7.93 min., carbon disulfide 8.64 min., and the three cogeners of allyl methyl sulfide 13.41, 13.87, and 14.37 min.

The distributions of the clinical chemistry and breath data were found to be non-normally distributed for the study subjects with liver diseases, and therefore, statistical analyses of the data were performed using non parametric tests (Wilcoxon, and Krusial-Wallis). However, if the raw data were logarithmically transformed, the resulting data were normally distributed and parametric tests such as the t-test, analysis of variance, multiple comparison tests (Bonferroni and Scheffe tests), linear regression, multiple regression and logistic regression could be used to investigate the transformed data.

Initially, the differences between the means of the clinical chemistry data for the study subjects with liver disease and the means of the clinical chemistry data for the study subjects with normal liver function were examined by means of non-parametric tests with the raw data and parametric tests with the log-transformed data. The results of parametric tests (t-test) are shown in Table 2 (below), together with the means and standard deviations for the raw data. As expected, the means of the clinical chemistry data, with the exception of serum urea nitrogen, for study subjects with liver diseases were significantly different from those for study subjects with normal liver function.

TABLE 2

Summary of the results of comparisons (t-test based on the log transformed data) for various measurements between study subjects with normal and abnormal liver function

| TEST COMPARISSON | NORMAL | BILE DUCT | |
|---|---|---|---|
| SERUM | | | |
| alanine aminotransferase (IU/L) | 21 (14)* | 93 (18) | <0.00001** |
| almumin (g/dL) | 4.6 (0.3) | 3.6 (0.3) | <0.00001 |
| alkaline phosphatase (IU/L) | 71 (20) | 220 (20) | <0.00001 |
| aspartate aminotransferase (IU/L) | 22 (6) | 120 (21) | <0.00001 |
| total bilirubin (mg/dL) | 0.8 (0.4) | 5.7 (0.9) | <0.00001 |
| total cholesterol (mg/dL) | 186 (40) | 164 (8) | 0.0001 |
| urea nitrogen (mg/dL) | 14 (4) | 18 (2) | 0.07 |
| BREATH | | | |
| Carbon disulfide (pmol/L) | 966 (1063) | 952 (293) | 0.22 |
| carbonyl sulfide (pmol/L) | 3778 (1660) | 7121 (3358) | <0.00001 |
| dimethyl sulfide (pmol/L) | 2341 (2363) | 6183 (1426) | 0.05 |
| ethane (pmol/L) | 118 (134) | 175 (77) | 0.017 |
| isoprene (pmol/L) | 5975 (2264) | 6398 (365) | 0.64 |

*mean (standard deviation) of raw data
**p value

When the various molecules detected in exhaled breath were examined, the mean of the concentrations of carbonyl sulfide found in the breath of study subjects with liver diseases were found to be significantly different from that found in the breath of normal subjects. The mean concentrations of ethane and dimethyl sulfide found in the breath of study subjects with liver diseases were also different from the concentration found in the breath of normal subjects. No significant differences were observed between the concentrations of isoprene, carbon disulfide or acetone found in the breath of these two study groups. These results are summarized in Table 2.

Three additional sulfur-containing molecules were identified in the breath of the study subjects. The molecules were the congeners of allyl methyl sulfide and were present in the breath of study subjects who had eaten foods containing garlic. These molecules are shown in FIG. 3 (retention times: 13.41, 13.87, and 14.37 min). The rates of clearance of these volatile sulfides from the breath were found to be subject-dependent but not liver disease-dependent.

Since the study population did not have a sufficient number of subjects diagnosed to have specific liver diseases to allow statistical analyses to be performed by disease state, our study subjects with liver diseases were stratified into two populations: study subjects with hepatocellular injury (alcoholic cirrhosis, α-1antitypsin deficiency, autoimmune cirrhosis, cryptogenic cirrhosis, fulminant hepatitis, hepatitis B and C, and steatohepatitis) and study subjects with diseases of the bile duct (cystic fibrosis, primary biliary cirrhosis, sclerosing cholangitis and biliary obstruction). The differences between the means of the clinical and breath data for these two study populations were compared individually to normal subjects. The results of these comparisons (t-tests using log-transformed data) are shown in Tables 3 and 4. As expected, significant differences were seen in the means of the clinical chemistry data for study subjects with hepatocellular injury, and with diseases of the bile duct compared to subjects with normal liver function.

Tables 3 and 4 are provided below.

TABLE 3

Summary of the results of comparisons (t-test based on the log-transformed data) for various measurements between normal subjects and study subjects and study subjects with hepatocellular injury

| TEST COMPARISSON | NORMAL | BILE DUCT | |
|---|---|---|---|
| SERUM | | | |
| alanine aminotransferase (IU/L) | 21 (14)* | 96 (185) | <0.00001** |
| almumin (g/dL) | 4.6 (0.3) | 3.7 (2.6) | <0.00001 |
| alkaline phosphatase (IU/L) | 71 (20) | 168 (94) | <0.00001 |
| aspartate aminotransferase (IU/L) | 22 (6) | 126 (224) | <0.00001 |
| total bilirubin (mg/dL) | 0.8 (0.4) | 4.9 (7.1) | <0.00001 |
| total cholesterol (mg/dL) | 186 (40) | 151 (500) | 0.0001 |
| BREATH | | | |
| carbonyl sulfide (pmol/L) | 3778 (1660) | 445 (604) | <0.00001 |
| dimethyl sulfide (pmol/L) | 2341 (2363) | 7136 (1484) | 0.045 |
| ethane (pmol/L) | 118 (134) | 211 (813) | 0.02 |

*mean (standard deviation) of raw data
*p value

TABLE 4

Summary of the results of comparisons (t-test based on the log-transformed data) for various measurements between normal subjects and study subjects with injury of the bile duct

| TEST COMPARISSON | NORMAL | BILE DUCT | |
|---|---|---|---|
| SERUM | | | |
| alanine aminotransferase (IU/L) | 21 (14)* | 85 (65) | <0.00001** |
| almumin (g/dL) | 4.6 (0.3) | 3.3 (0.9) | <0.00001 |
| alkaline phosphatase (IU/L) | 71 (20) | 391 (9275) | <0.00001 |
| aspartate aminotransferase (IU/L) | 22 (6) | 102 (60) | <0.00001 |
| total bilirubin (mg/dL) | 0.8 (0.4) | 8.2 (11.6) | <0.00001 |
| BREATH | | | |
| carbonyl sulfide (pmol/L) | 3778 (1660) | 445 (604) | <0.00001 |

*mean (standard deviation) of raw data
**p value

The mean level of carbonyl sulfide in the breath of study subjects with hepatocellular injury was significantly elevated compared to the mean level found in the breath of normal subjects. The differences between the mean breath ethane and breath dimethyl sulfide levels for these two study groups were also significant. It is interesting to note that the mean concentration of carbonyl sulfide in the breath of subjects with diseases of the bile duct was significantly lower than those with normal liver function (Table 4) while the mean concentration of breath carbonyl sulfide of the subjects with hepatocellular injury was significantly higher than those with normal liver function. There were no significant differences between the mean concentrations of either breath ethane or breath dimethyl sulfide for study subjects with diseases of the bile duct compared to normals.

The clinical chemistry and breath data for normals and for subjects with hepatacellular injury and separately for study subjects with diseases of the bile duct were examined as a function of severity of liver disease using analysis of variance (ANOVA) and comparisons of means. Table 5 (below) shows the summary of the analysis of variance for the various measurements as a function of severity of liver disease (staging). With the exception of serum urea nitrogen, the serum chemistries showed significant differences as liver disease progressed. The means of the serum chemistries increased (cholesterol decreased) as liver disease became more severe. Only breath carbonyl sulfide was found to be significantly different for both disease groups.

TABLE 5

Summary of the analysis of variance (based on the log-transformed data) for various measurements of hepatocellular and bile duct injury as a function of severity of liver disease

| Test | Hepatocellular | Bile Duct |
|---|---|---|
| SERUM | | |
| alanine aminotransferase (IU/L) | <0.00001* | <0.00001 |
| almumin (g/dL) | <0.00001 | <0.00001 |
| alkaline phosphatase (IU/L) | <0.00001 | <0.00001 |
| aspartate aminotransferase (IU/L) | <0.00001 | <0.00001 |
| total bilirubin (mg/dL) | <0.00001 | <0.00001 |
| total cholesterol (mg/dL) | <0.00001 | <0.00001 |
| urea nitrogen (mg/dL) | 0.026 | 0.0001 |
| BREATH | | |
| carbon disulfide (pmol/L) | 0.20 | 0.14 |
| carbonyl sulfide (pmol/L) | <0.00001 | <0.00001 |
| dimethyl sulfide (pmol/L) | 0.01 | 0.4 |
| ethane (pmol/L) | 0.03 | 0.9 |
| isoprene (pmol/L) | 0.07 | 0.2 |

*p value

Figure 4:
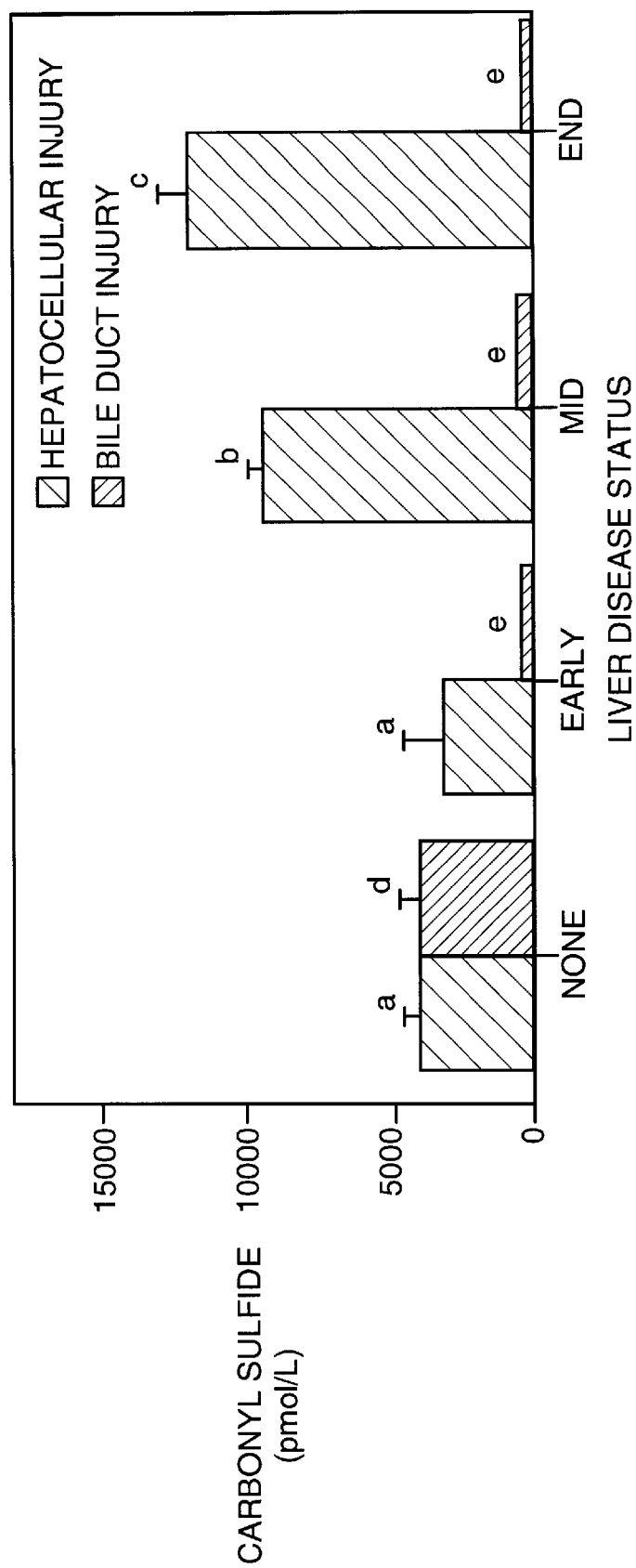
FIG. 4 is a graph showing breath carbonyl sulfide examined as a function of severity of liver disease for hepatocellular and bile duct injury using analysis of variance and comparisons of means.

The data for breath carbonyl sulfide (mean and standard error of raw data) as a function of liver disease staging are shown in FIG. 4 (Table 5). Breath concentrations of carbonyl sulfide increased with staging for the study subjects with hepatocellular injury and decreased as a function of staging in the patients with diseases of the bile duct. Increases with the severity of the disease were also observed for dimethyl sulfide in the study group with hepatocellular injury (Table 5 and FIG. 5) whereas no statistically significant differences were observed for the stage of liver disease in the study group that had diseases of the bile duct. Levels of breath ethane were the only other breath biomarker that showed any statistical significance as a function of staging in these study subjects. There was a highly significant increase in breath ethane for those study subjects with hepatocellular injury (Table 5 and FIG. 6) at mid-stage disease and this increase may reflect inflammation that subsequently decreases as the liver becomes more cirrhotic.

FIG. 4 is more particularly explained as follows: Results were expressed as mean and standard error of the raw data The letters a, b, and c are for hepatocellular injury and d, and e are for bile duct injury, data with the same letter are not statistically different. No hepatocellular injury n=109; early-stage hepatocellular injury n=14; mid-stage hepatocellular injury n=27; end-stage hepatocellular injury n=25; no bile duct injury n=1–9; early-stage bile duct injury n=6; mid-stage bile duct injury n=11; end-stage bile duct injury n=3.

Figure 5:
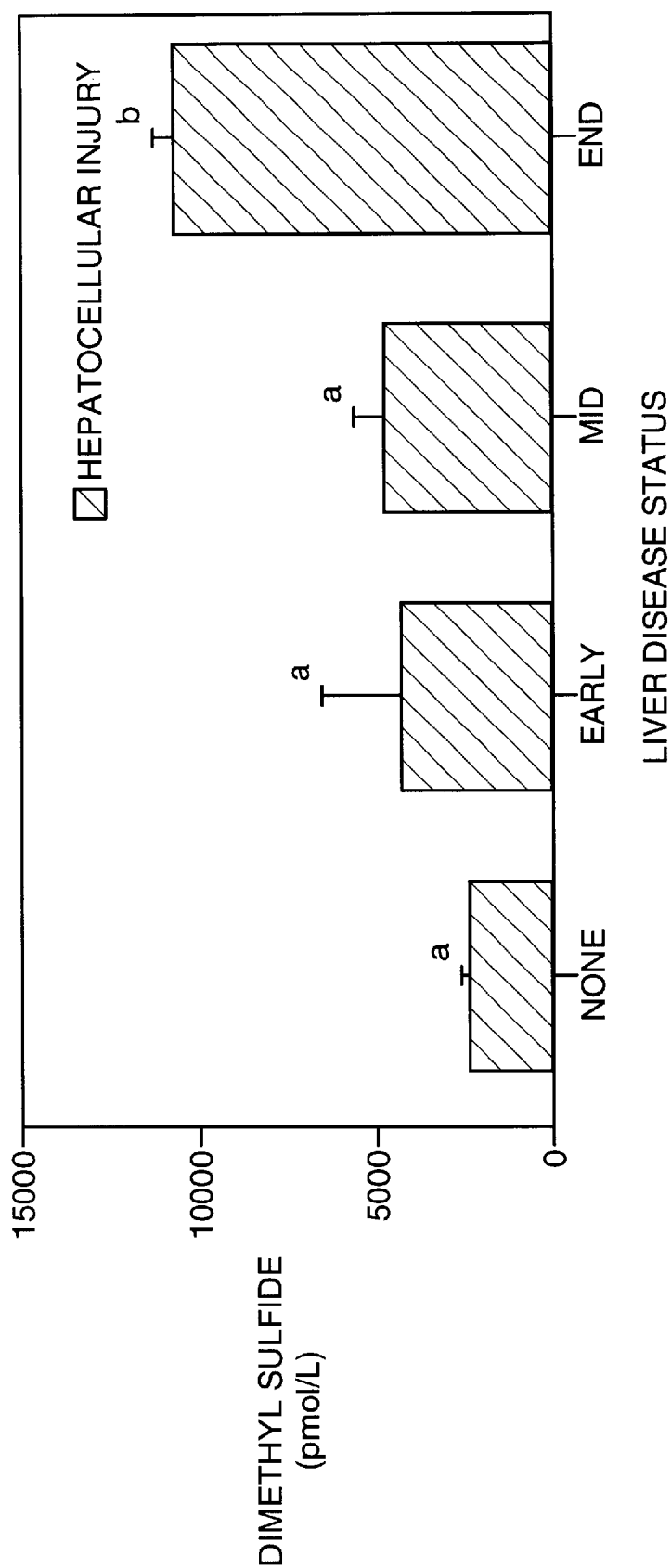
FIG. 5 is a graph showing breath dimethyl sulfide examined as a function of severity of liver disease for heptocellular injury using analysis of variance and comparisons of means.

FIG. 5 is more specifically explained as follows: Results were expressed as mean and standard error of the raw data. The letters a, and b are for hepatocellular injury, data with the same letter are not statistically different. No hepatocellular injury n=109; early-stage hepatocellular injury n=14; mid-stage hepatocellular injury n=27; end-stage hepatocellular injury n=25.

Figure 6:
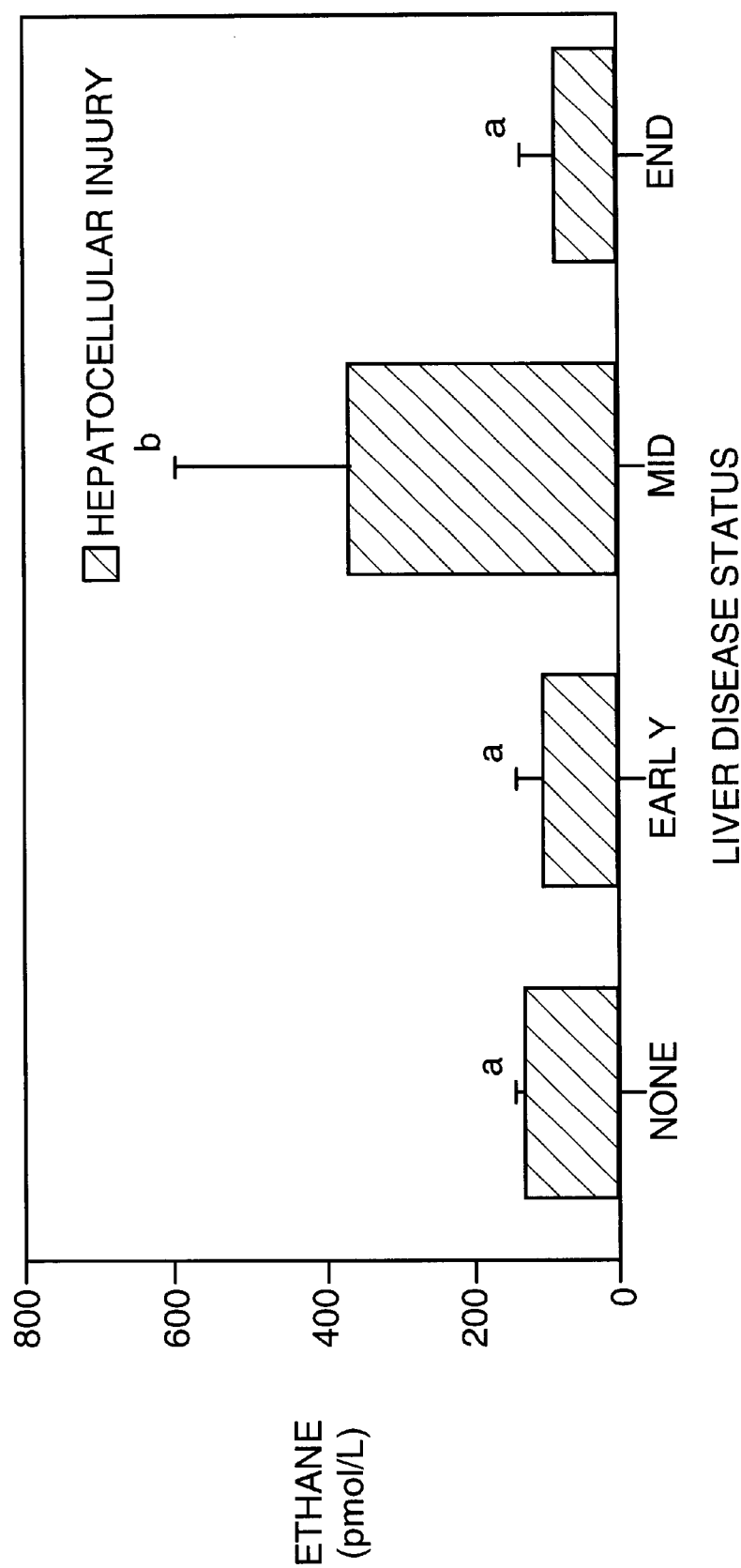
FIG. 6 is a graph illustrating breath ethane examined as a function of severity of liver disease for hepatocellular injury using analysis of variance and comparisons of means.

FIG. 6 is explained in more detail as follows: Results were expressed as mean and standard error of the raw data. The letters a, and b are for hepatocellular injury, data with the same letter are not statistically different. No hepatocellular injury n=109; early-stage hepatocellular injury n=14; mid-stage hepatocellular injury n=27; end-stage hepatocellular injury n=25.

Figure 7:
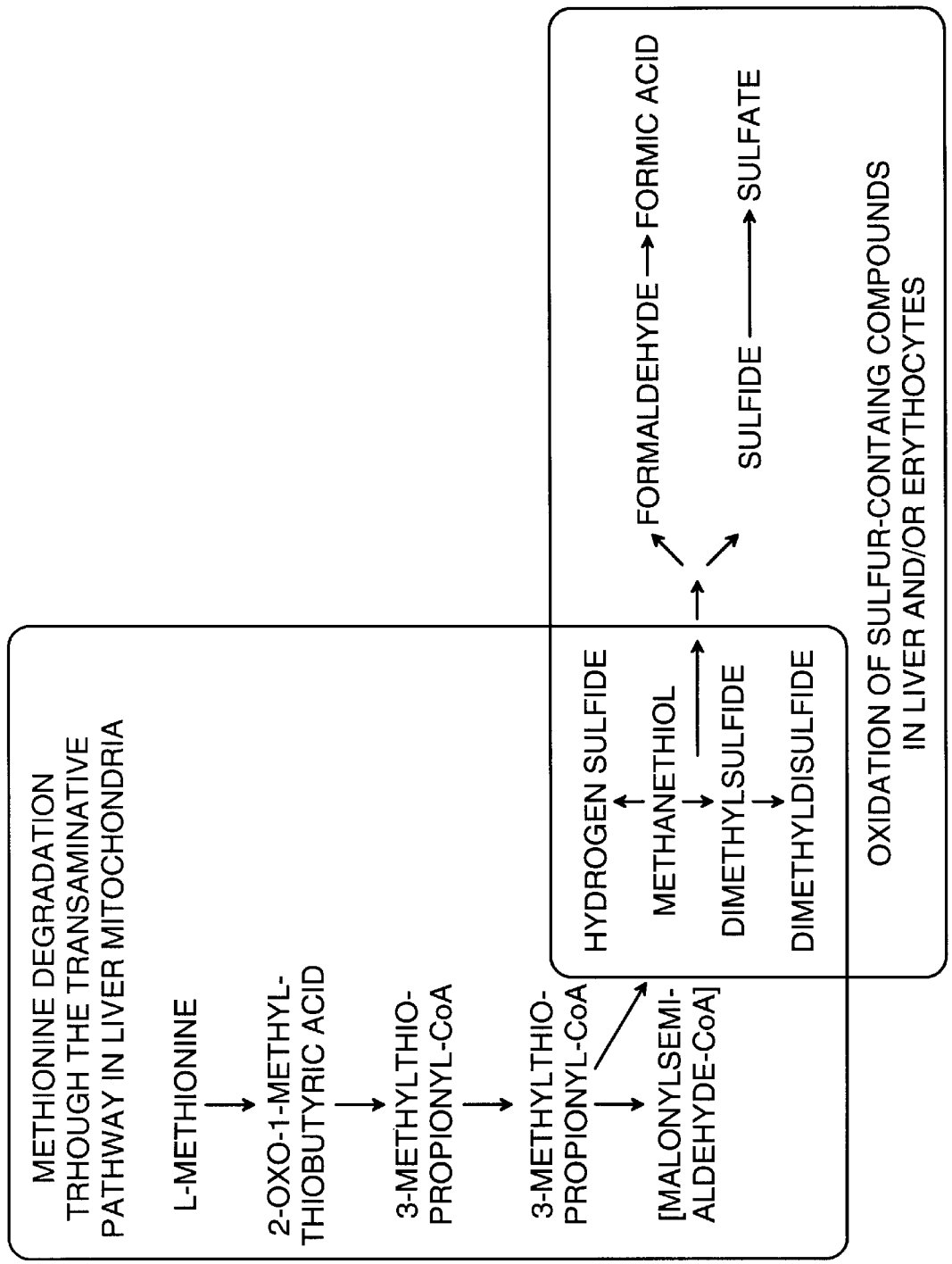
FIG. 7 is a schematic summary of biological pathways that form certain volatile sulfur containing compounds.

No changes in breath sulfur containing compounds have been found in subjects with other diseases, including cardiac diseases, renal disease and hyperlipidemias. FIG. 7 provides a summary of methionine metabolism in the liver.

DISCUSSION

Carbon disulfide has been identified in breath of human subjects receiving disulfiram (bis(diethylthiocarbamoyl) disulfide) as aversion therapy for chronic alcoholism. See e.g., Phillips et al., *Alcoh. Clin. Exp. Red.,* (1992), 16: 964. However, none of the present subjects were receiving disulfiram therapy and the levels of the carbon disulfide were not statistically significantly different between study groups. Moreover, no correlation was found between the levels of breath carbon disulfide and the levels of other volatile sulfur-containing compounds detected in breath. It is unlikely that the origin of breath carbonyl sulfide is the oxidative metabolism of carbon disulfide since no correlation between these two molecules in exhaled breath was found. There was a correlation between the levels of exhaled breath methyl sulfide and the levels of breath carbonyl sulfide. This correlation suggests that carbonyl sulfide may also be produced during the incomplete metabolism sulfur containing of essential systems including methionine (see FIG. 7).

Without wishing to be bound to theory, one interpretation of the data suggests that the precursors of carbonyl sulfide are excreted in bile and gut bacterial action is responsible for carbonyl sulfide production. Levels of breath carbonyl sulfide decrease as a function of disease status in those study subjects that presented diseases of the bile duct. Bile duct disease reduces the production of bile. The observation that the levels of dimethyl sulfide were not comparably reduced with severity of biliary duct dysfunction suggests that the production of carbonyl sulfide and dimethyl sulfide do not share a complete common pathway. It is possible that dimethyl sulfide (and/or methanethiol) may be oxidized by gut bacterial action to carbonyl sulfide. The statistically significant increases in the levels of breath ethane for study subjects with hepatocellular injury judged to have mid-stage liver disease supports the proposition that hepatocellular injury involves oxygen-free radical mediated inflammation.

The following materials and methods were used as needed in the foregoing examples.

1. Human studies

Research was approved by The Johns Hopkins Joint Committee on Clinical investigation. Samples were collected from consenting adults (50 males, 36 females) who attended a Liver Clinic at the Johns Hopkins Hospital and from normal adult volunteers (65 males, 44 females) with similar age and race distributions.

2. Blood collection

A blood sample, drawn via venopuncture into a vacutainer tube, was collected from each study subject. Breath and blood samples were collected simultaneously.

3. Room Air Collection

Room air was sampled with a glass syringe at the time of breath collection and stored in gas-tight collection bags (3L, Calibrated Instruments Inc., Ardsley, N.Y.). These samples were used to determine the background concentrations of the analyte molecules.

4. Storage of Gaseous Samples

Our previous research has shown that breath and room air samples are stable in gas collection bags for at least 48 hours, although all samples were analyzed within 6–8 hours of collection.

5. Liver function and other clinical tests

The blood samples collected from each study subject were submitted for the following analyses: serum urea nitrogen, serum total bilirubin, serum alanine aminotransferase, serum aspartate aminotransferase, serum alkaline phosphatase, serum albumin, differential white blood cell count, and total serum cholesterol. These tests were performed in the clinical chemistry laboratories of The Johns Hopkins Hospital using standard assays.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A test system for detecting a hepatic disorder in a mammal, the test system comprising:
   a) a chamber for receiving respiratory gas from the mammal; and
   b) a monitor for detecting at least one volatile organic molecule in the respiratory gas and for outputting the concentration of at least one of the detected organic molecules, wherein the monitor comprises or is interfaced with at least one of:
      i) a computational system adapted to correlate the concentration of at least one of the detected organic molecules (test value) to at least one of a pre-determined control or analytical value, or
      ii) a carbon dioxide analyzer for correcting the concentration of at least one of the detected molecules to an alveolar concentration of carbon dioxide.

2. The test system of claim 1, wherein the test system is adapted to stage the hepatic disorder and the output is a display in real-time.

3. A test system for detecting and staging a hepatic disorder in a mammal, the test system comprising:
   a) a gas collection apparatus for receiving respiratory gas from the mammal and for outputting volatile organic molecules in the gas,
   b) a chromatography system for receiving the volatile organic molecules from the apparatus and for detecting volatile organic molecules comprising at least one of hydrocarbon or organosulfur molecule; and
   c) a computational system adapted to process output from the chromatography system, wherein the computational system performs the following steps:
      i) determine the concentration of volatile organic molecules detected by the chromatography system,
      ii) correlate the concentration of at least one of the detected organic molecules to at least one of a pre-determined analytical or control value for the molecule, and
      iii) output results.

4. The test system of claim 3, wherein the gas collection apparatus has a sampling volume of from between about 0.01 liters to 20 liters.

5. The test system of claim 3, wherein the chromatography system comprises a pair of detectors for detecting the hydrocarbon or sulfur.

6. The test system of claim 3, wherein computational system is adapted to correct the concentration of the volatile organic molecules to an alveolar concentration of carbon dioxide.

7. The test system of claim 3, wherein the pre-determined analytical value is the mean concentration of the molecule in respiratory gas collected from mammals suffering from the presence and stage of the hepatic disorder.

8. The test system of claim 3, wherein the predetermined control value is the mean concentration of the molecule in respiratory gas collected from normal mammals.

9. The test system of claim 3, wherein the computation system is adapted to perform a parametric test between the concentration of the detected organic molecule and the pre-determined analytical or control value.

10. The test system of claim 6, wherein the computational system is adapted to output at least one of the following: the alveolar concentration of carbon dioxide, the concentration of the volatile organic molecule, the pre-determined analytical or control value, or control and results of a parametric test.

11. The test system of claim 7, wherein the pre-determined analytical or control value is the mean concentration of ethane, carbonyl sulfide or dimethyl sulfide in the respiratory gas samples.

12. The test system of claim 3, wherein the hepatic disorder is hepatocellular injury or a biliary tract disorder.

13. A method for detecting and staging a hepatic disorder in a mammal, the method comprising:
   a) collecting respiratory gas from the mammal,
   b) determining the concentration of at least one volatile organic molecule in the respiratory gas; and
   c) correlating the concentration of the volatile organic molecule to presence and stage of the hepatic disorder in the mammal, the method further comprising correcting the concentration of the organic molecule to an alveolar concentration of carbon dioxide.

14. The method of claim 13, wherein the respiratory gas is collected into a gas collection apparatus having a sampling volume of from between about 0.01 liters to 20 liters.

15. The method of claim 13, wherein prior to determining the concentration, the volatile organic molecules are separated on a chromatography system capable of detecting at least one of hydrocarbon or sulfur.

16. The method of claim 15, wherein the chromatography system comprises a pair of detectors for detecting hydrocarbon or sulfur.

17. The method of claim 12, wherein the detected organic molecule is ethane, carbonyl sulfide, or dimethyl sulfide.

18. The method of claim 12, wherein the hepatic disorder is hepatocellular injury or a biliary tract disorder.

19. A method for detecting and staging a hepatic disorder in a mammal, the method comprising:
   a) collecting respiratory gas from the mammal into a gas collection apparatus,
   b) separating the respiratory gas on a first gas chromatograph comprising a first detector capable of detecting hydrocarbon,
   c) detecting ethane in the released molecules,
   d) separating the respiratory gas on a second gas chromatograph comprising a second detector capable of detecting organosulfur molecules,
   e) detecting at least one of carbonyl sulfide or dimethyl sulfide in the released molecules; and
   f) correlating the concentration of at least one of ethane, carbonyl sulfide or dimethyl sulfide to presence and stage of the hepatic system disorder in the mammal.

20. The method of claim 19, wherein the gas collection apparatus has a sampling volume of from between about 0.01 liters to 20 liters.

21. The method of claim 20, wherein the gas collection apparatus comprises a chamber comprising a polymeric adsorbent and the method further comprises cooling the chamber from between about $-100°$ C. to $-150°$ C. to concentrate the volatile organic molecules in the adsorbent.

22. The method of claim 21, wherein the method further comprises heating the chamber from between about $100°$ C. to $200°$ C. to release the concentrated volatile organic molecules therefrom.

23. The method of claim 19, wherein the hepatic disorder is hepatocellular injury or a biliary tract disorder.

24. A method for detecting a hepatic disorder in a mammal, the method comprising:
   a) collecting respiratory gas from the mammal,
   b) determining concentration of carbonyl sulfide in the respiratory gas; and
   c) correlating the concentration of carbonyl sulfide to the presence of the hepatic disorder in the mammal, the method further comprising correcting the concentration of carbonyl sulfide to an alveolar concentration of carbon dioxide.

25. The method of claim 24, wherein prior to determining the concentration, the respiratory gas is separated on a chromatographic system capable of detecting hydrocarbon and organosulfur molecules.

26. The method of claim 25, wherein the chromatography system comprises a pair of detectors for detecting the hydrocarbon or organosulfur molecules.

27. The method of claim 25, wherein the respiratory gas is collected into a gas collection apparatus having a sampling volume of from between about 0.01 liters to 20 liters.

28. The method of claim 24, wherein the hepatic disorder is hepatocellular injury or a biliary tract disorder.

29. A method for detecting hepatocellular injury or a biliary tract disorder in a mammal, the method comprising:
   a) collecting respiratory gas from the mammal,
   b) determining concentration of at least one of ethane, carbonyl sulfide, or dimethyl sulfide in the respiratory gas; and
   e) correlating the concentration of at least one of the ethane, carbonyl sulfide or dimethyl sulfide to the presence of the hepatocellular injury or the biliary tract disorder in the mammal, the method further comprising correcting the concentration of the ethane, carbonyl sulfide or dimethyl sulfide to an alveolar concentration of carbon dioxide.

30. The method of claim 29, wherein prior to determining the concentration, the respiratory gas is separated on a chromatographic system capable of detecting hydrocarbon and organosulfur molecules.

31. The method of claim 30, wherein the chromatography system comprises a pair of detectors for detecting the hydrocarbon or organosulfur molecules.

32. The test system of claim 1, wherein the monitor comprises a mass spectrometer.

33. The test system of claim 32, wherein the mass spectrometer is an infra-red (IR) sensitive spectrometer or a gas chromatography-mass spectrometer (GC-MS).

34. The test system of claim 33, wherein the infra-red (IR) sensitive spectrophotometer is a mid-IR laser absorption spectrophotometer equipped with a Harriott multi-pass cell, the laser being a lead-salt tunable diode laser (TDL).

35. The test system of claim 32, wherein the computational system is further adapted to receive output from the mass spectrometer and to provide output in real-time to a user of the test system.

36. The test system of claim 1 in which the computational system is further adapted to receive input from the monitor and to output data to a user of the test system, wherein the monitor receives respiratory gas provided by a human subject.

37. A method for detecting and staging a hepatic disorder in a mammal, the method comprising:
   a) collecting respiratory gas from the mammal,
   b) determining the concentration of at least one volatile organic molecule in the respiratory gas; and
   c) correlating the concentration of the volatile organic molecule to presence and stage of the hepatic disorder in the mammal, wherein the respiratory gas is collected into a gas collection apparatus having a sampling volume of from between about 0.01 liters to 20 liters, the gas collection apparatus comprising a chamber comprising a polymeric adsorbent, wherein the method further comprises cooling the chamber from between about −100° C. to −150° C. to concentrate the volatile organic molecules in the adsorbent.

38. A method for detecting and staging a hepatic disorder in a mammal, the method comprising:
   a) collecting respiratory gas from the mammal,
   b) determining the concentration of at least one volatile organic molecule in the respiratory gas; and
   c) correlating the concentration of the volatile organic molecule to presence and stage of the hepatic disorder in the mammal, wherein the respiratory gas is collected into a gas collection apparatus having a sampling volume of from between about 0.01 liters to 20 liters, the gas collection apparatus comprising a chamber comprising a polymeric adsorbent, wherein the method further comprises cooling the chamber from between about −100° C. to −150° C. to concentrate the volatile organic molecules in the adsorbent and heating the chamber from between about 100° C. to 200° C. to release the concentrated volatile organic molecules therefrom.

39. A method for detecting and staging a hepatic disorder in a mammal, the method comprising:
   a) collecting respiratory gas from the mammal,
   b) determining the concentration of at least one volatile organic molecule in the respiratory gas; and
   c) correlating the concentration of the volatile organic molecule to presence and stage of the hepatic disorder in the mammal, wherein the correlation step further comprises correcting the concentration of the organic molecule to an alveolar concentration of carbon dioxide.

40. A method for detecting and staging a hepatic disorder in a mammal, the method comprising:
   a) collecting respiratory gas from the mammal,
   b) determining the concentration of at least one volatile organic molecule in the respiratory gas; and
   c) correlating the concentration of the volatile organic molecule to presence and stage of the hepatic disorder in the mammal, wherein the correlating step further comprises comparing the concentration to a pre-determined analytical value indicative of presence and stage of the hepatic disorder in the mammal.

41. A method for detecting and staging a hepatic disorder in a mammal, the method comprising:
   a) collecting respiratory gas from the mammal,
   b) determining the concentration of at least one volatile organic molecule in the respiratory gas; and
   c) correlating the concentration of the volatile organic molecule to presence and stage of the hepatic disorder in the mammal, wherein the correlating step further comprises comparing the concentration to a pre-determined analytical value indicative of presence and stage of the hepatic disorder in the mammal and the pre-determined analytical value is the mean concentration of the organic molecule in respiratory gas collected from mammals suffering from the presence and stage of the hepatic disorder.

42. A method for detecting and staging a hepatic disorder in a mammal, the method comprising:
   a) collecting respiratory gas from the mammal,
   b) determining the concentration of at least one volatile organic molecule in the respiratory gas; and
   c) correlating the concentration of the volatile organic molecule to presence and stage of the hepatic disorder in the mammal, wherein the correlating step further comprises comparing the concentration to a pre-determined control value indicative of normal hepatic function.

43. A method for detecting and staging a hepatic disorder in a mammal, the method comprising:
   a) collecting respiratory gas from the mammal,
   b) determining the concentration of at least one volatile organic molecule in the respiratory gas; and
   c) correlating the concentration of the volatile organic molecule to presence and stage of the hepatic disorder in the mammal, wherein the correlating step further comprises comparing the concentration to a pre-determined control value indicative of normal hepatic function and the control value is the mean concentration of the organic molecule in respiratory gas collected from normal mammals.

44. A method for detecting and staging a hepatic disorder in a mammal, the method comprising:
   a) collecting respiratory gas from the mammal,
   b) determining the concentration of at least one volatile organic molecule in the respiratory gas; and
   c) correlating the concentration of the volatile organic molecule to presence and stage of the hepatic disorder in the mammal, wherein the correlating step further comprises comparing the concentration to a pre-determined analytical value indicative of presence and stage of the hepatic disorder in the mammal, the correlating step further comprising performing a parametric test between the concentration of the detected organic molecule and the pre-determined analytical or control value.

45. A method for detecting a hepatic disorder in a mammal, the method comprising:
   a) collecting respiratory gas from the mammal,
   b) determining concentration of carbonyl sulfide in the respiratory gas; and
   c) correlating the concentration of carbonyl sulfide to the presence of the hepatic disorder in the mammal, wherein prior to determining the concentration, the respiratory gas is separated on a chromatographic system capable of detecting hydrocarbon and organosulfur molecules, the chromatography system comprising a pair of detectors for detecting the hydrocarbon or organosulfur molecules and further wherein the respiratory gas is collected into a gas collection apparatus having a sampling volume of from between about 0.01 liters to 20 liters, the gas collection apparatus comprising a chamber comprising a polymeric adsorbent, the method further comprising cooling the chamber from between about −100° C. to −150° C. to concentrate the volatile organic molecules in the adsorbent.

46. A method for detecting a hepatic disorder in a mammal, the method comprising:
    a) collecting respiratory gas from the mammal,
    b) determining concentration of carbonyl sulfide in the respiratory gas; and
    c) correlating the concentration of carbonyl sulfide to the presence of the hepatic disorder in the mammal, wherein prior to determining the concentration, the respiratory gas is separated on a chromatographic system capable of detecting hydrocarbon and organosulfur molecules, the chromatography system comprising a pair of detectors for detecting the hydrocarbon or organosulfur molecules and further wherein the respiratory gas is collected into a gas collection apparatus having a sampling volume of from between about 0.01 liters to 20 liters, the gas collection apparatus comprising a chamber comprising a polymeric adsorbent, the method further comprising cooling the chamber from between about −100° C. to −150° C. to concentrate the volatile organic molecules in the adsorbent and heating the chamber from between about 100° C. to 200° C. to release the concentrated volatile organic molecules therefrom.

47. A method for detecting hepatocellular injury or a biliary tract disorder in a mammal, the method comprising:
    a) collecting respiratory gas from the mammal,
    b) determining concentration of at least one of ethane, carbonyl sulfide, or dimethyl sulfide in the respiratory gas; and
    c) correlating the concentration of at least one of the ethane, carbonyl sulfide or dimethyl sulfide to the presence of the hepatocellular injury or the biliary tract disorder in the mammal, wherein prior to determining the concentration, the respiratory gas is separated on a chromatographic system capable of detecting hydrocarbon and organosulfur molecules, the chromatography system comprising a pair of detectors for detecting the hydrocarbon or organosulfur molecules and further wherein the respiratory gas is collected into a gas collection apparatus having a sampling volume of from between about 0.01 liters to 20 liters.

48. A method for detecting hepatocellular injury or a biliary tract disorder in a mammal, the method comprising:
    a) collecting respiratory gas from the mammal,
    b) determining concentration of at least one of ethane, carbonyl sulfide, or dimethyl sulfide in the respiratory gas; and
    c) correlating the concentration of at least one of the ethane, carbonyl sulfide or dimethyl sulfide to the presence of the hepatocellular injury or the biliary tract disorder in the mammal, wherein prior to determining the concentration, the respiratory gas is separated on a chromatographic system capable of detecting hydrocarbon and organosulfur molecules, the chromatography system comprising a pair of detectors for detecting the hydrocarbon or organosulfur molecules and further wherein the respiratory gas is collected into a gas collection apparatus having a sampling volume of from between about 0.01 liters to 20 liters, the gas collection apparatus comprising a chamber comprising a polymeric adsorbent and the method further comprises cooling the chamber from between about −100° C. to −150° C. to concentrate the volatile organic molecules in the adsorbent.

49. A method for detecting hepatocellular injury or a biliary tract disorder in a mammal, the method comprising:
    a) collecting respiratory gas from the mammal,
    b) determining concentration of at least one of ethane, carbonyl sulfide, or dimethyl sulfide in the respiratory gas; and
    c) correlating the concentration of at least one of the ethane, carbonyl sulfide or dimethyl sulfide to the presence of the hepatocellular injury or the biliary tract disorder in the mammal, wherein prior to determining the concentration, the respiratory gas is separated on a chromatographic system capable of detecting hydrocarbon and organosulfur molecules, the chromatography system comprising a pair of detectors for detecting the hydrocarbon or organosulfur molecules and further wherein the respiratory gas is collected into a gas collection apparatus having a sampling volume of from between about 0.01 liters to 20 liters, the gas collection apparatus comprising a chamber comprising a polymeric adsorbent and the method further comprises cooling the chamber from between about −100° C. to −150° C. to concentrate the volatile organic molecules in the adsorbent, wherein the method further comprises heating the chamber from between about 100° C. to 200° C. to release the concentrated volatile organic molecules therefrom.

50. The method of claim 49, wherein the method further comprises staging the hepatocellular injury or biliary tract disorder in the mammal.

51. The test system of claim 1, wherein the monitor is adapted to detect chemiluminescence or Raman scattering.

52. The test system of claim 1, wherein the monitor can further detect at least one of NO, CO, $CO_2$, $N_2O$, $NH_3$, $C_2H_6$, or $H_2O_2$.

53. The test system of claim 1, wherein the volatile organic molecule is carbonyl sulfide, hydrogen sulfide, methyl sulfide, dimethyl sulfide, allyl methyl sulfide; or a cogener thereof.

54. The test system of claim 33, wherein the chamber is adapted to include an infra-red (IR) source.

55. The test system of claim 1, wherein the mammal is a human.

56. The method of claim 13, 19, 24, or 29, wherein the mammal is a human.

* * * * *